(12) United States Patent
Metuki

(10) Patent No.: US 9,737,813 B2
(45) Date of Patent: Aug. 22, 2017

(54) COGNITIVE TRAINING METHOD FOR SEMANTIC SKILLS ENHANCEMENT

(71) Applicant: Nili Metuki, Even-Yehuda (IL)

(72) Inventor: Nili Metuki, Even-Yehuda (IL)

(73) Assignee: Nili Metuki, New York, NY (US)

( * ) Notice: Subject to any disclaimer, the term of this patent is extended or adjusted under 35 U.S.C. 154(b) by 178 days.

(21) Appl. No.: 14/399,253

(22) PCT Filed: May 7, 2013

(86) PCT No.: PCT/IL2013/050390
§ 371 (c)(1),
(2) Date: Nov. 6, 2014

(87) PCT Pub. No.: WO2013/168154
PCT Pub. Date: Nov. 14, 2013

(65) Prior Publication Data
US 2015/0140525 A1  May 21, 2015

Related U.S. Application Data

(60) Provisional application No. 61/643,350, filed on May 7, 2012.

(51) Int. Cl.
*A63F 13/63* (2014.01)
*A63F 13/44* (2014.01)
(Continued)

(52) U.S. Cl.
CPC .............. *A63F 13/63* (2014.09); *A63F 13/44* (2014.09); *A63F 13/46* (2014.09); *G06Q 50/20* (2013.01);
(Continued)

(58) Field of Classification Search
USPC ........................................................ 434/169
See application file for complete search history.

(56) References Cited

U.S. PATENT DOCUMENTS

| 4,607,848 A | 8/1986 | Maguire et al. |
| 2002/0107062 A1 | 8/2002 | Wong |

(Continued)

FOREIGN PATENT DOCUMENTS

WO  WO 2013/168154  11/2013

OTHER PUBLICATIONS

International Preliminary Report on Patentability dated Nov. 20, 2014 From the International Bureau of WIPO Re. Application No. PCT/IL2013/050390.

(Continued)

*Primary Examiner* — Kesha Frisby

(57) ABSTRACT

A method for training a semantic ability of a subject, the method being performed by a computer the method comprising: a. Displaying a linguistic task to the subject on a display of the computer, said linguistic task comprising providing one or more words, wherein said linguistic task is directed to training the subject in a specific semantic skill or skills; b. Providing a plurality of linguistic clues to the subject, through the display of the computer, said plurality of linguistic clues comprising content capable of activating concepts related to said one or more words but wherein said content does not include said one or more words or synonyms thereof, wherein said linguistic clues are selected such that the subject integrates said plurality of linguistic clues to solve said linguistic task, wherein said linguistic clue comprises an image, audio, video, text or a combination thereof; c. Receiving a solution to said linguistic task by the subject through the computer; and d. If said solution is not correct, providing one or more additional linguistic clues to the subject, said one or more additional linguistic clues comprising content capable of activating concepts related to said one or more words, wherein the subject integrates said one or more additional linguistic clues with said plurality of (Continued)

linguistic clues to solve said linguistic task, and wherein i) said content does not include said one or more words or synonyms thereof, or ii) if said content does include said one or more words or synonyms thereof, said content does not comprise written text.

13 Claims, 34 Drawing Sheets

(51) Int. Cl.
*A63F 13/46* (2014.01)
*G06Q 50/20* (2012.01)
*G06Q 90/00* (2006.01)
*G09B 5/06* (2006.01)
*G09B 19/00* (2006.01)
*G06F 19/00* (2011.01)

(52) U.S. Cl.
CPC ............... *G06Q 90/00* (2013.01); *G09B 5/06* (2013.01); *G09B 19/00* (2013.01); *A63F 2300/305* (2013.01); *A63F 2300/513* (2013.01); *A63F 2300/552* (2013.01); *A63F 2300/554* (2013.01); *A63F 2300/6027* (2013.01); *A63F 2300/61* (2013.01); *A63F 2300/8064* (2013.01); *G06F 19/3481* (2013.01)

(56) References Cited

U.S. PATENT DOCUMENTS

2007/0011005 A1   1/2007   Morrison et al.
2011/0256513 A1   10/2011   Levitt et al.

OTHER PUBLICATIONS

International Search Report dated Sep. 9, 2013 From the International Searching Authority Re. Application No. PCT/IL2013/050390.

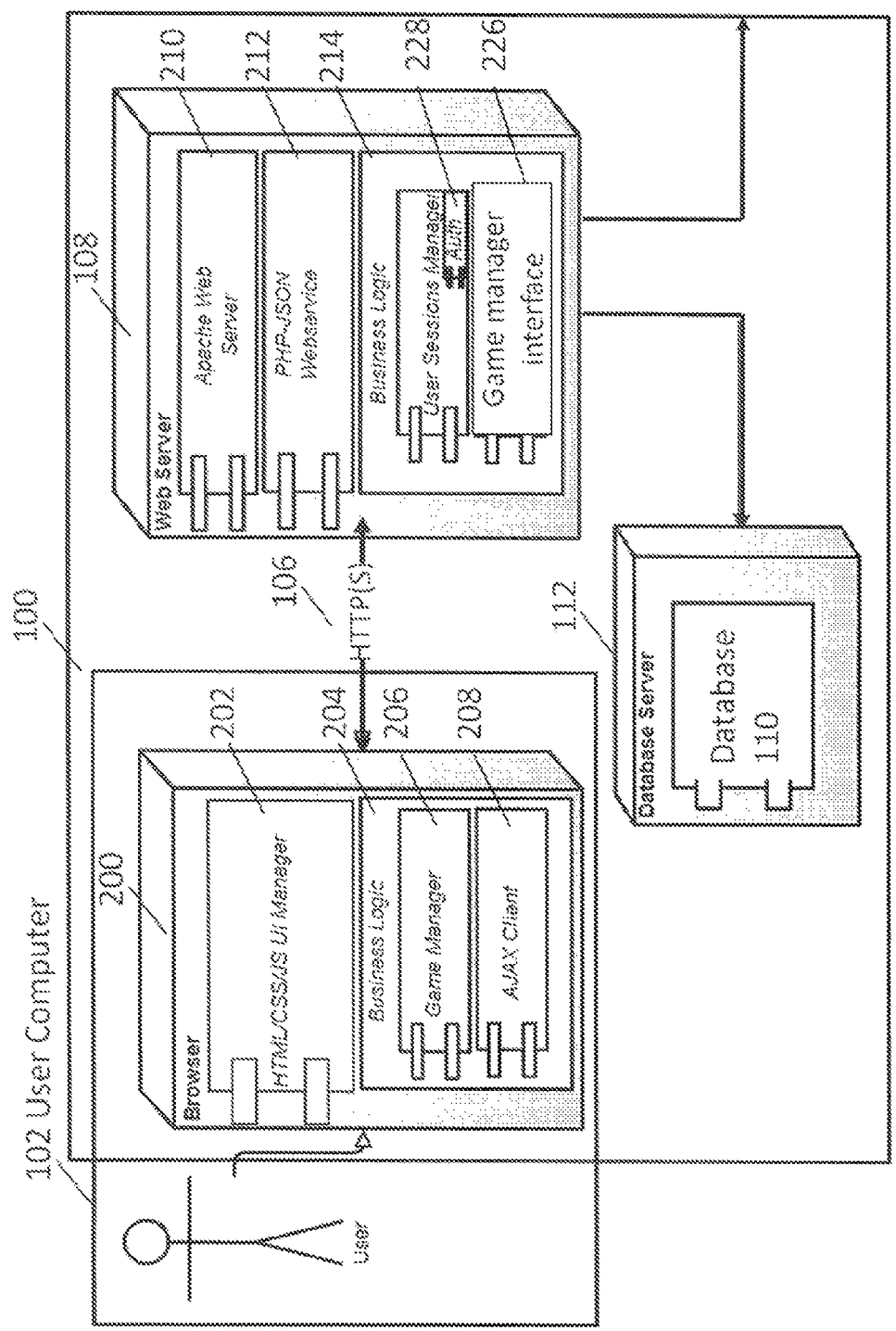

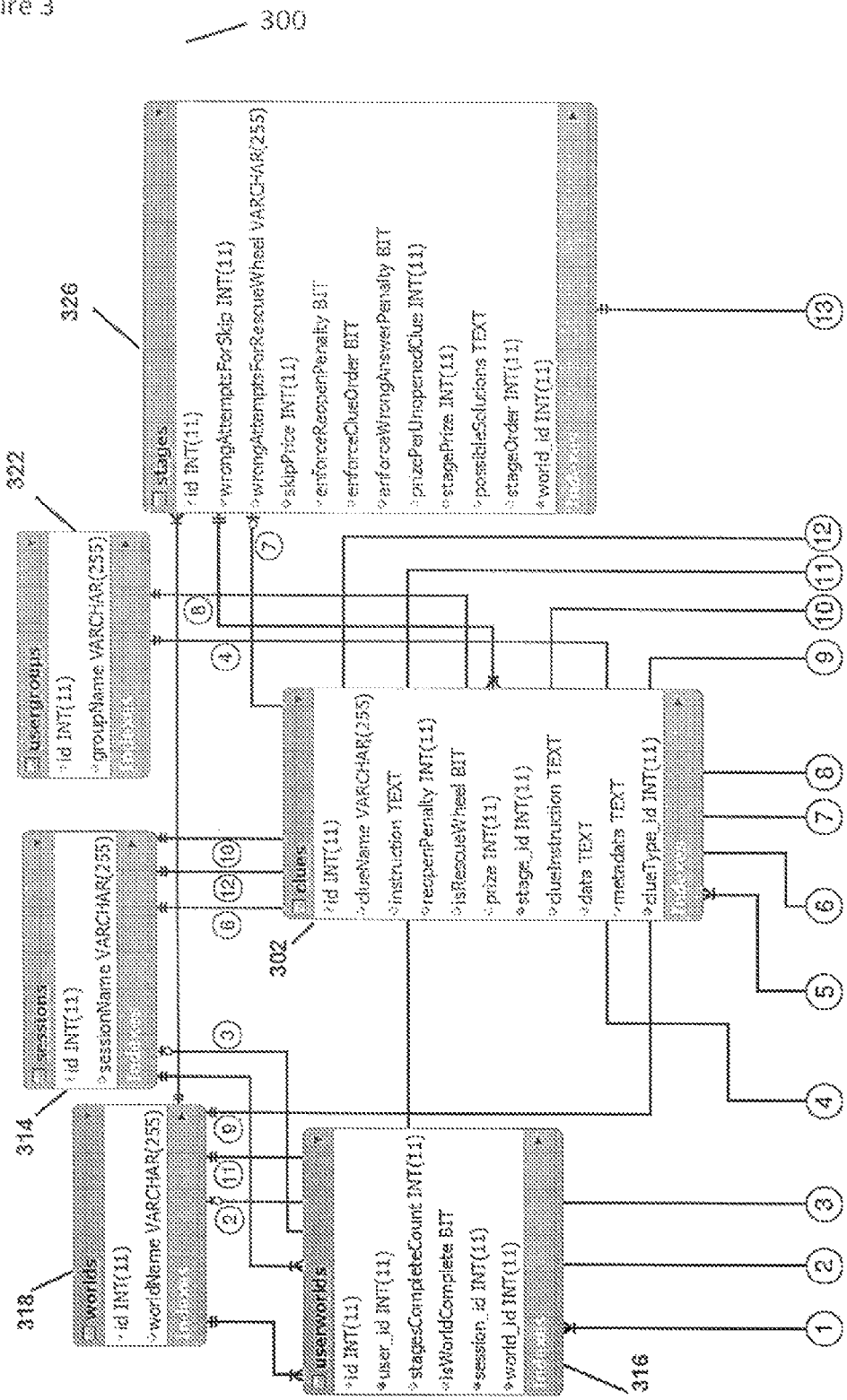

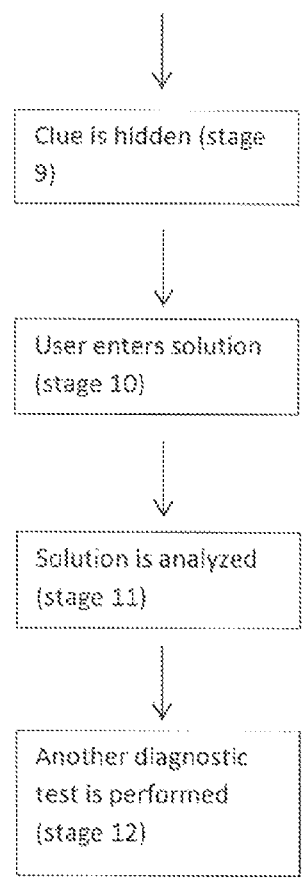
Figure 5 (con't)

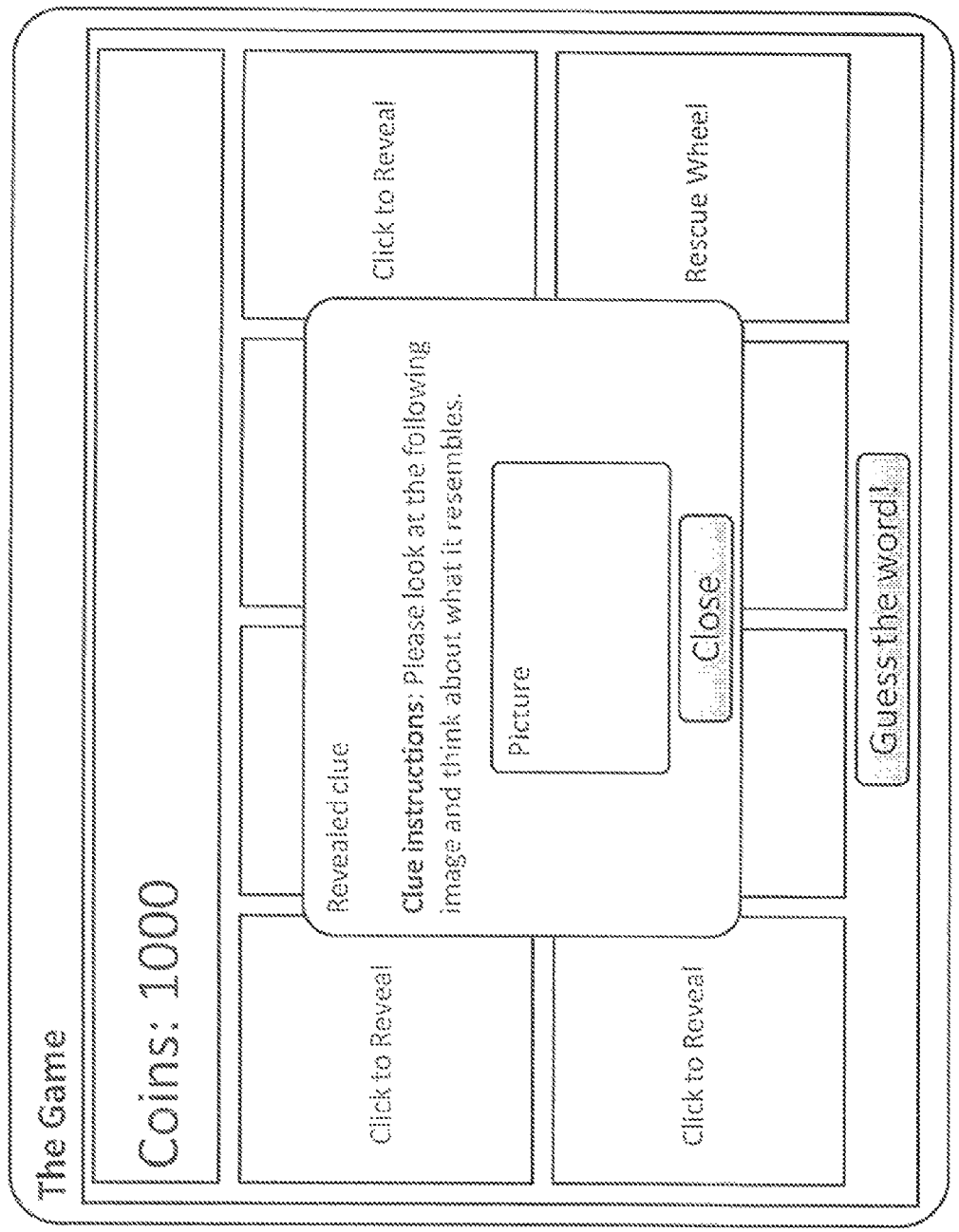

Figure 9

Table 1

*An Example for the Clues in One of the First Levels on "Word Game", and Their Relations to the Solution Word*

| Clues | Relation between clue and solution word (day) |
|---|---|
| In Greek Mythology, Hemera is the daughter of Nyx (goddess of the night) and Erebos (the personification of darkness). | Hamera is the goddess of the day. Other concepts mentioned in the description (night) are also associated with day. |
|  | This is a typicle picture of a birthday party, with a birthday cake. The concept of birthday is clearly related to day. |
| Sunrise | Sunrise is associated with day. |
| 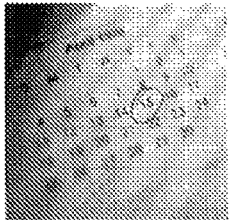 | This is a picture of a day marked on a calander. |

Figure 10

Table 2
*Group Comparisons across Various Background Measurements, as Measured Prior to Participation and Analyzed by Independent Samples t-tests*

| Variable | Measurement | Training group Mean (SD) | Control group Mean (SD) | Group differences |
|---|---|---|---|---|
| Age | Years of age | 23.27 (1.71) | 23.67 (2.55) | $t(28) = -0.50$ $p = .618$ |
| Education | Years of education | 13.33 (1.18) | 13.33 (1.29) | $t(28) = 0.00$ $p = 1$ |
| Handedness | Laterality Quotient - Edinburgh handedness inventory (Oldfield, 1971) | 92.78 (11.29) | 97.26 (5.77) | $t(21) = -1.37$ $p = .185$ |
| Avoidance motivation | BIS (behavioral inhibition system) score (Carver & White, 1994) | 14.00 (3.12) | 13.33 (3.94) | $t(28) = 0.51$ $p = .611$ |
| Approach motivation | BAS (behavioral activation system) score (Carver & White, 1994) | 24.80 (5.23) | 22.80 (5.07) | $t(28) = 1.06$ $p = .297$ |
| Reward sensitivity | BAS reward (Carver & White, 1994) | 8.33 (2.74) | 7.40 (1.72) | $t(28) = 1.12$ $p = .274$ |
| Scholastic | Overall Psychometric Entrance Test score | 674.43 | 681.00 | $t(25) = -0.38$ |

Figure 10 (cont.)

| | | | | |
|---|---|---|---|---|
| abilities | (Beller, 1995) | (35.70) | (53.29) | $p = .708$ |
| Hebrew vocabulary & reasoning | Verbal reasoning score-PET (Beller, 1995) | 130.00 (12.07) | 134.00 (13.58) | $t(21) = -0.73$ $p = .471$ |

Figure 11

Table 3
*Group Comparison of Baseline Performance across Tasks, as Measured on the Pre-training Assessment Session and Analyzed by Independent Samples t-tests*

| Task | Measurement | Training group Mean (SD) | Control group Mean (SD) | Group differences |
|---|---|---|---|---|
| Semantic task: relatedness judgments following ambiguous prime words | RT/ACC | 11.51 (2.64) | 11.00 (2.08) | $t(28) = 0.59$ $p = .561$ |
| Verbal memory test: subset of Rey Auditory Verbal Learning Test (AVLT) | Immediate memory | 7.47 (1.64) | 7.60 (2.61) | $t(28) = -0.167$ $p = .868$ |
| | Best memory | 13.27 (1.22) | 13.87 (0.92) | $t(28) = -1.52$ $p = .139$ |
| | Learning rate | 5.80 (1.70) | 6.27 (2.82) | $t(23) = -0.55$ $p = .588$ |
| | Total memory | 55.87 (5.58) | 58.73 (5.22) | $t(28) = -1.45$ $p = .157$ |
| Lexical task: lexical decision | RT/ACC - Words only | 9.81 (1.34) | 9.11 (1.61) | $t(28) = 1.284$ $p = .210$ |
| Non-verbal task: lateralized Coherent motion detection (CMD) | Coherency thresholds | 0.79 (0.14) | 0.77 (0.12) | $t(28) = 0.38$ $p = .709$ |

Figure 11 (cont.)

| | | | | |
|---|---|---|---|---|
| Laterality index: Line Bisection[1] | Arcsin transformation of individual averaged percentage deviation | 0.00 (0.10) | 0.05 (0.10) | $t(26) = -1.40$ $p = .173$ |

*Note.* [1]The line bisection task baseline reflects performance on the first training session.

Figure 13

Table 4

*Raw Pre and Post-Training Scores in the Three Semantic Task Relation Type Conditions, by Performance Measurement and Group*

| Relation type | Time of measurement | RT / ACC | | RT | | ACC | |
|---|---|---|---|---|---|---|---|
| | | Training group Mean (SD) | Control group Mean (SD) | Training group Mean (SD) | Control group Mean (SD) | Training group Mean (SD) | Control group Mean (SD) |
| Dominant | Pre-training | 9.66 (2.61) | 9.24 (2.31) | 782.32 (137.59) | 782.46 (127.52) | 83.00 (9.78) | 86.33 (9.35) |
| | Post-training | 8.03 (1.48) | 8.85 (1.51) | 702.85 (118.03) | 734.42 (105.05) | 88.00 (7.02) | 83.67 (7.43) |
| Subordinate | Pre-training | 13.26 (3.96) | 10.74 (2.48) | 876.08 (178.62) | 835.71 (137.97) | 68.33 (11.75) | 79.33 (9.42) |
| | Post-training | 10.53 (2.37) | 10.64 (1.74) | 794.52 (161.18) | 797.13 (122.61) | 76.67 (11.6) | 75.67 (9.42) |
| Unrelated | Pre-training | 12.04 (3.61) | 12.29 (3.08) | 1012.75 (235.89) | 1008.68 (151.07) | 85.67 (7.88) | 84.17 (9.90) |
| | Post-training | 11.16 (3.64) | 10.51 (2.28) | 964.11 (236.62) | 949.11 (152.75) | 88.33 (8.54) | 91.50 (6.99) |

Figure 14

Table 5

*Raw Pre and Post-Training Scores in the Four Verbal Memory Test Scores, and the Results of Mixed ANOVA Examining Time of Measurement and Group Effect on Each Score*

|  | Pre-training | | Post-training | | ANOVA | | |
| --- | --- | --- | --- | --- | --- | --- | --- |
|  | Training Group | Control Group | Training Group | Control Group | Time | Group | Time X Group |
| Test score | Mean (SE) | Mean (SE) | Mean (SE) | Mean (SE) | $F(1,28)$ | $F(1,28)$ | $F(1,28)$ |
| Immediate memory | 7.47 (0.56) | 7.60 (0.56) | 8.67 (0.52) | 8.13 (0.52) | 7.00* | $F<1$ | 1.04 |
| Best memory | 13.27 (0.28) | 13.87 (0.28) | 14.20 (0.23) | 14.27 (0.23) | 8.78** | 1.43 | 1.40 |
| Learning rate | 5.80 (0.60) | 6.27 (0.60) | 5.53 (0.58) | 6.13 (0.58) | $F<1$ | $F<1$ | $F<1$ |
| Total memory | 55.87 (1.39) | 58.73 (1.39) | 60.07 (1.55) | 60.13 (1.55) | 5.34* | $F<1$ | 1.33 |

*Note.* * $p < .05$, ** $p < .01$

Figure 16

Table 6

*Raw Pre and Post-Training Scores in the Three Lexical Task Presentation Conditions, by Performance Measurement and Group*

| Condition | Time of measurement | RT / ACC | | RT | | ACC | |
|---|---|---|---|---|---|---|---|
| | | Training group Mean (SD) | Control group Mean (SD) | Training group Mean (SD) | Control group Mean (SD) | Training group Mean (SD) | Control group Mean (SD) |
| Center | Pre-training | 7.42 (0.78) | 7.11 (0.86) | 689.56 (69.84) | 675.93 (75.83) | 93.00 (4.93) | 95.33 (4.81) |
| | Post-training | 6.91 (0.82) | 7.28 (0.96) | 666.68 (67.90) | 676.25 (86.00) | 96.67 (3.62) | 93.00 (3.16) |
| lvf-RH | Pre-training | 11.79 (4.02) | 10.19 (3.61) | 904.78 (68.88) | 827.56 (93.99) | 81.33 (15.86) | 85.67 (14.98) |
| | Post-training | 10.95 (3.18) | 11.89 (8.53) | 884.49 (96.81) | 852.46 (77.82) | 84.00 (12.42) | 84.67 (20.31) |
| rvf-LH | Pre-training | 11.56 (2.51) | 11.51 (4.18) | 908.06 (74.49) | 874.36 (102.33) | 80.67 (12.08) | 80.67 (14.62) |
| | Post-training | 12.26 (3.22) | 11.43 (3.28) | 887.61 (109.33) | 879.19 (100.27) | 75.33 (13.43) | 80.33 (13.56) |

Figure 18

Table 7

*Raw Pre and Post-Training Scores in the Two Non-Verbal Task Visual-Field Conditions, by Group*

| Condition | Time of measurement | Training group Mean (SD) | Control group Mean (SD) |
|---|---|---|---|
| lvf-RH | Pre-training | 0.82 (0.14) | 0.78 (0.12) |
|  | Post-training | 0.70 (0.12) | 0.68 (0.14) |
| rvf-LH | Pre-training | 0.76 (0.16) | 0.76 (0.14) |
|  | Post-training | 0.67 (0.14) | 0.64 (0.15) |

Figure 19

Table 8

*Summary of Training Gains Compared by Group, across the Four Tests Included in the Test-Retest Battery*

| Task | Individual change measurement | Group differences | Group * Type interactions | Conclusions |
|---|---|---|---|---|
| Semantic task | RT/ACC | $F(1,28) = 2.37$ | $F(2,56) = 4.13*$ | Training gain in judging semantic relatedness of distantly related meanings for ambiguous words, but not for unrelated meanings. |
| Verbal memory test | Immediate memory | $F < 1$ | $F(1,28) = 1.04$ | Gain in verbal memory for both training and control programs; Semantic training did not induce additional benefits. |
| | Best memory | $F(1,28) = 1.43$ | $F(1,28) = 1.40$ | |
| | Learning rate | $F < 1$ | $F < 1$ | |
| | Total learning | $F < 1$ | $F(1,28) = 1.33$ | |
| Lexical task | RT/ACC - Words only | $F < 1$ | $F(2,56) = 1.40$ | Training did not induce improvement in recognizing words (not even words presented to the lvf-RH). |

Figure 19 (cont.)

| Non-verbal task | Coherency thresholds | $F < 1$ | $F(1,28) = 1.16$ | Training did not induce improvement in coherent motion detection (not even in the lvf-RH) |
|---|---|---|---|---|

Note. * $p < .05$

Figure 20

Table 9

*Individual Laterality Shifts, and Average Deviations from the Midpoint in the Line Bisection Task in the First and Last Training Sessions, by Group*

| Group | Individual shift Mean (*SD*) | First session Mean (*SD*) | Last session Mean (*SD*) |
|---|---|---|---|
| Training Group | -2.43% (15.17) | 0.07% (9.83) | 4.27% (13.14) |
| Control Group | -3.50% (6.28) | 5.43% (10.40) | 9.33% (9.49) |

*Note.* Mean deviations are calculated as arcsin transformation of the average percent of deviation from the line midpoint in each of the sessions, averaged across participants and trials; Positive deviation indicates an LH bias.

Figure 21

Table 10

*Regression Coefficients and Significance for a Series of Six Analyses: Each Analysis Used Laterality Shift to Predict the Individual Performance Change in One of the Three Conditions of the Semantic Task, in Each Group Separately*

| Group | Predicted variable: individual change | B | SE (B) | β | t | $R^2$ | $F(1, 12)$ |
|---|---|---|---|---|---|---|---|
| Training group | Subordinate relation type condition | 91.51 | 31.54 | 0.642 | 2.90* | 41.2% | 8.42* |
| | Dominant relation type condition | -7.37 | 35.59 | -0.060 | -0.21 | 0.4% | $F<1$ |
| | Unrelated condition | -37.23 | 34.85 | -0.295 | -1.07 | 8.7% | 1.14 |
| Control group | Subordinate relation type condition | -118.41 | 94.69 | -0.340 | -1.25 | 11.5% | 1.56 |
| | Dominant relation type condition | -72.52 | 76.98 | -0.262 | -0.94 | 6.9% | $F<1$ |
| | Unrelated condition | -58.07 | 97.31 | -0.170 | -0.60 | 2.9% | $F<1$ |

*Note.* * $p < .05$

Figure 22

Table 11

*Regression Coefficients and Significance for a Series of Six Analyses: Each Analysis Used Verbal Reasoning PET Score to Predict the Individual Performance Change in One of the Three Conditions of the Semantic Task, in Each Group Separately.*

| Group | Predicted variable: individual change | B | SE (B) | β | t | $R^2$ | F |
|---|---|---|---|---|---|---|---|
| Training group | Subordinate relation type condition | 1.30 | 0.50 | 0.679 | 2.62* | 46.1% | $F(1,8) = 6.84$* |
| | Dominant relation type condition | -0.06 | 0.37 | -0.058 | -0.16 | 0.3% | $F < 1$ |
| | Unrelated condition | 1.10 | 0.80 | 0.436 | 1.37 | 19.0% | $F(1,8) = 1.88$ |
| Control group | Subordinate relation type condition | -0.78 | 0.47 | -0.448 | -1.66 | 20.0% | $F(1,11) = 2.76$ |
| | Dominant relation type condition | -0.42 | 0.36 | -0.329 | -1.15 | 10.8% | $F(1,11) = 1.33$ |
| | Unrelated condition | -0.41 | 0.48 | -0.248 | -0.85 | 6.1% | $F < 1$ |

*Note.* * $p < .05$

Figure 23

Table 12

*Regression Coefficients and Significance for a Series of Two Analyses: Each Analysis Used Reward Sensitivity (BAS-RR Score) to Predict the Individual Performance Change for the Subordinate Relation Type Condition in the Semantic Task, in Each Group Separately*

| Group | $B$ | $SE(B)$ | $\beta$ | $t$ | $R^2$ | $F(1, 13)$ |
|---|---|---|---|---|---|---|
| Training group | -1.71 | 2.06 | -0.225 | -0.83 | 5.0% | 0.69 |
| Control group | -7.76 | 2.86 | -0.602 | -2.72* | 36.2% | 7.38* |

Note. * $p < .05$

COGNITIVE TRAINING METHOD FOR SEMANTIC SKILLS ENHANCEMENT

RELATED APPLICATIONS

This application is a National Phase of PCT Patent Application No. PCT/IL2013/050390 having International filing date of May 7, 2013, which claims the benefit of priority under 35 USC §119(e) of U.S. Provisional Patent Application No. 61/643,350 filed on May 7, 2012. The contents of the above applications are all incorporated by reference as if fully set forth herein in their entirety.

FIELD OF THE INVENTION

The present invention, in at least some embodiments, relates to a system and method for training the semantic ability or abilities of a subject.

BACKGROUND OF THE INVENTION

Applications of accumulated knowledge in cognitive psychology have led to the creation of different interventions to improve cognitive performance in real life settings. In particular, applied research has demonstrated that cognitive performance in various domains can be enhanced by non-invasive computerized cognitive training programs (Green & Bavelier, 2008; Willis et al., 2006). While most computerized cognitive training studies have focused on cognitive skills related to memory, attention and executive functions, few reports have documented attempts that are aimed to improve linguistic abilities in general, and language comprehension in particular, among literate adults.

Nevertheless, in recent years much progress has been achieved in the understanding of underlying neuro-cognitive processes of language comprehension. As opposed to the outdated notion that all language functions are exclusively lateralized to the left hemisphere (LH), it is now clear that semantic processing in the right hemisphere (RH) has a unique contribution to language comprehension and creative aspects of language (for reviews, see Beeman & Chiarello, 1998; Kahlaoui, Scherer, & Joanette, 2008; Lindell, 2006; Mitchell & Crow, 2005).

Numerous conceptualization efforts have been made in order to account for the asymmetric lateralization of language processing in the brain (for review, see Dien, 2008). Jung-Beeman (2005) has suggested the BAIS model (Bilateral Activation, Integration and Selection) as a comprehensive theoretical framework for the recent findings on the hemispheric asymmetry in semantic processing. According to the model, bilateral semantic processes of activation, integration and selection interact in order to process language.

According to the BAIS model (Jung-Beeman, 2005), the RH coarse semantic processing patterns (diffused semantic activation, leading to weak activation of multiple concepts remotely associated to the input, followed by their integration and selection) are efficient for natural language comprehension, verbal creativity and similar high-order skills that require the person to integrate distant and initially irrelevant information. Fine LH semantic processing patterns (rapid activation, focused on dominant features which are tightly linked to the input, followed by efficient integration and selection) are crucial for most language comprehension tasks, as well as for language production, as they benefit from the quick activation and selection of contextual relevant salient meanings—but are less effective when multiple or less salient meanings are required. For example, when participants generate a typical use for a noun (e.g., airplane—fly) the LH is more involved, but when requested to generate an unusual use (e.g., airplane—build) higher involvement is detected in the RH (Seger, Desmond, Glover, & Gabrieli, 2000). Accordingly, as argued by Jung-Beeman, coarse semantic coding patterns underlie higher level linguistic tasks, such as inference drawing, metaphor and humor comprehension, as well as message level comprehension tasks (deriving themes, generating optimal sentence endings, determining narrative sequence and inconsistencies) (Jung-Beeman, 2005; on the notion of coarse and fine semantic coding see also Beeman et al., 1994, Beeman, 1998).

Accumulated publications of controlled cognitive training studies have demonstrated that the learning of new cognitive skills and the improvement of existing skills is possible across different populations and ages. For instance, numerous studies have been successful in enhancing cognitive skills in older adults, with or without mild cognitive impairments (for reviews, see Jean, Bergeron, Thivierge, & Simard, 2010; Valenzuela & Sachdev, 2009). The success of training has also been documented in clinical populations, including patients with schizophrenia (for reviews, see McGurk, Twamley, Sitzer, McHugo, & Mueser, 2007; Twamley, Jeste, & Bellack, 2003) and children with ADHD (for review, see Toplak et al., 2008).

More than a few studies have shown long lasting effects of cognitive training, as well as the generalization of the trained skill in daily untrained tasks (also termed 'transfer', see Blume, Ford, Baldwin, & Huang, 2010). Unlike other instructional interventions, cognitive training programs engage participants in tasks that stimulate target cognitive processes, allowing participants to explore and acquire new strategies while handling the training tasks, and later use the acquired skills flexibly in untrained tasks. For example, a study with air force pilots, healthy young adults, demonstrated improved real-time flight performance following training on the 'space fortress' game (Gopher, Weil, & Bareket, 1994; Hart & Battiste, 1992). A comprehensive clinical trial (n=2832) identified long term effects of cognitive training in healthy older adults, which were expressed in trained skills (memory, reasoning and processing speed) as well as in untrained daily functions, for at least five years after training (Willis et al., 2006). A computer assisted training program for children with ADHD resulted in significant improvements in attention as well as in non-trained academic measures (Shalev, Tsal, & Mevorach, 2007).

Moreover, cognitive training effects are not limited to changes in behavioral performance. Several brain imaging studies have recently revealed training-induced plasticity in the healthy human brain (i.e., Dahlin, Neely, Larsson, Bäckman, & Nyberg, 2008; Erickson et al., 2007; McNab et al., 2009; Olesen, Westerberg, & Klingberg, 2004).

While the aforementioned studies did lead to the transfer of the trained skills into other tasks and situations, other cognitive training studies did not result in transfer effects. Recent reviews of computerized cognitive training programs show that controlled empirical evidence for transfer is limited, due to different causes related to the interventions themselves, the trainability of the target skills, and study design (Green & Bavelier, 2008; Melby-Lervåg & Hulme, 2012; Shipstead, Redick, & Engle, 2010).

While preliminary evidence suggests some promise for linguistic training, the question remains whether cognitive training could induce the improvement of linguistic skills in non-trained linguistic tasks in larger samples.

SUMMARY OF THE INVENTION

The background art does not teach or suggest an effective system and method for determining the semantic ability of a subject, and/or for training or improving this semantic ability, whether in normal subjects or in subjects with a deficit in one or more semantic abilities.

The present invention, in at least some embodiments, overcomes these drawbacks of the background art by providing an effective system and method for determining the semantic ability of a subject, as well for training or improving this semantic ability, whether in normal subjects or in subjects with a deficit in one or more semantic abilities.

According to at least some embodiments of the present invention, there is provided a method for training a semantic ability of a subject, the method being performed by a computer, the method comprising:

a. Displaying a linguistic task to the subject on a display of the computer, said linguistic task comprising providing one or more words, wherein said linguistic task is directed to training the subject in a specific semantic skill or skills;

b. Providing a plurality of linguistic clues to the subject, through the display of the computer, said plurality of linguistic clues comprising content capable of activating concepts related to said one or more words but wherein said content does not include said one or more words or synonyms thereof, wherein said linguistic clues are selected such that the subject integrates said plurality of linguistic clues to solve said linguistic task, wherein said linguistic clue comprises an image, audio, video, text or a combination thereof;

c. Receiving a solution to said linguistic task by the subject through the computer; and d. If said solution is not correct, providing one or more additional linguistic clues to the subject, said one or more additional linguistic clues comprising content capable of activating concepts related to said one or more words, wherein the subject integrates said one or more additional linguistic clues with said plurality of linguistic clues to solve said linguistic task, and wherein i) said content does not include said one or more words or synonyms thereof, or ii) if said content does include said one or more words or synonyms thereof, said content does not comprise written text.

Optionally said providing one or more words by the subject comprises entering said one or more words to the computer.

Optionally said providing one or more words by the subject comprises identifying said one or more words by the subject.

Optionally said plurality of clues is revealed sequentially.

Optionally each clue is revealed separately, such that only one clue is revealed at a given time.

Optionally said providing said linguistic clues to the subject further comprises penalizing the subject if the subject requests display of a previously displayed clue.

Optionally said plurality of clues is revealed simultaneously.

Optionally said sequence is selected according to a requirement for integration of said plurality of linguistic clues by the subject.

Optionally said receiving said solution to said linguistic task comprises analyzing said solution and wherein said analyzing said solution further comprises analyzing a correctness of said solution and one or more of a time required to complete said solution, a number of clues provided to the subject before said solution is submitted, a number of guesses before the correct solution was submitted, a number of times previously seen clues were displayed again, or a combination thereof. Optionally the method comprises repeating stages a-d at least once.

Optionally at least one of said linguistic task, said one or more linguistic clues, the specific instructions or the scoring system is different upon repetition of stages a-d.

Optionally said providing said plurality of linguistic clues to the subject, through the display of the computer, further comprises selecting said linguistic clues according to a level of difficulty.

Optionally said level of difficulty is determined according to a semantic ability of the subject.

Optionally said providing said plurality of linguistic clues to the subject, through the display of the computer, further comprises selecting said linguistic clues according to a semantic ability of the subject to be improved.

Optionally the method further comprises determining a semantic ability of the subject according to a diagnostic test.

Optionally a type of said diagnostic test is identical to a type of said diagnostic test of stage a.

Optionally said diagnostic test is identical to said diagnostic test of stage a but with different content.

Optionally a type of said diagnostic test is different from a type of said diagnostic test of stage a.

Optionally said diagnostic test comprises performing the method of stages a-d at least once.

Optionally said diagnostic test comprises performing a different diagnostic test other than the method of stages a-d.

Optionally said selecting said linguistic clues further comprises selecting a game world for the subject, said game world having a plurality of characteristic features, including at least one or more of instructions, incentives, type of clues, penalty on display of previous clues, sequence of clues and time of exposure of a given clue; and selecting said linguistic clues also according to said game world.

Optionally the method further comprises providing an incentive to the subject to provide said solution through the computer.

Optionally said incentive comprises one or more of points to obtain a reward, points convertible to monetary value, points relating to progress and/or points for comparison between different users.

According to at least some embodiments of the present invention, there is provided a method for determining semantic ability of a subject, the method being performed by a computer, the method comprising:

a. Displaying a linguistic task to the subject on a display of the computer, said linguistic task comprising providing one or more words by the subject to the computer;

b. Providing one or more linguistic clues to the subject, through the display of the computer, said one or more linguistic clues comprising content capable of activating concepts related to said one or more words but wherein i) said content does not include said one or more words or synonyms thereof, or ii) if said content does include said one or more words or synonyms thereof, said content does not comprise written text, wherein said linguistic clue comprises an image, audio, video, text or a combination thereof, and wherein said linguistic clues are selected such that the subject integrates said plurality of linguistic clues to solve said linguistic task;

c. Receiving a solution to said linguistic task by the subject through the computer; and d. Analyzing said solution to determine the semantic ability of the subject.

Optionally said providing one or more words by the subject comprises entering said one or more words to the computer.

Optionally said providing one or more words by the subject comprises identifying said one or more words by the subject.

Optionally said one or more linguistic clues comprises a plurality of clues and wherein said plurality of clues is revealed sequentially.

Optionally each clue is revealed separately, such that only one clue is revealed at a given time.

Optionally said sequence is selected according to a requirement for integration of said plurality of linguistic clues by the subject.

Optionally said providing one or more linguistic clues to the subject further comprises penalizing the subject if the subject requests display of a previously displayed clue.

Optionally said one or more linguistic clues comprises a plurality of clues and wherein said plurality of clues is revealed simultaneously.

Optionally said analyzing said solution further comprises analyzing a correctness of said solution and one or more of a time required to complete said solution or a number of clues provided to the subject before said solution is submitted.

Optionally the method comprises repeating stages a-d at least once.

Optionally said linguistic task and said one or more linguistic clues upon repetition of stages a-d are different.

Optionally said providing said plurality of linguistic clues to the subject, through the display of the computer, further comprises selecting said linguistic clues according to a level of difficulty.

Optionally said level of difficulty is determined according to a semantic ability of the subject.

Optionally said providing said plurality of linguistic clues to the subject, through the display of the computer, further comprises selecting said linguistic clues according to a semantic ability of the subject to be improved.

Optionally the method further comprises determining a semantic ability of the subject according to a diagnostic test.

Optionally a type of said diagnostic test is identical to a type of said diagnostic test of stage a.

Optionally said diagnostic test is identical to said diagnostic test of stage a but with different content.

Optionally a type of said diagnostic test is different from a type of said diagnostic test of stage a.

Optionally said diagnostic test comprises performing the method of stages a-d at least once.

Optionally said diagnostic test comprises performing a different diagnostic test other than the method of stages a-d.

Optionally said selecting said linguistic clues further comprises selecting a game world for the subject, said game world having a plurality of characteristic features, including at least one or more of instructions, incentives, type of clues, penalty on display of previous clues, sequence of clues and time of exposure of a given clue; and selecting said linguistic clues also according to said game world.

Optionally the method further comprises providing an incentive to the subject to provide said solution through the computer.

Optionally said incentive comprises one or more of points to obtain a reward, points convertible to monetary value, points relating to progress and/or points for comparison between different users.

According to at least some embodiments of the present invention, there is provided a method for training a semantic ability of a subject, the method being performed by a computer, the method comprising:

a. Displaying a linguistic task to the subject on a display of the computer, said linguistic task comprising providing one or more words;

b. Providing one or more linguistic clues to the subject, through the display of the computer, said one or more linguistic clues comprising content capable of activating concepts related to said one or more words but wherein said content does not include said one or more words or synonyms thereof, wherein said linguistic clue comprises an image, audio, video, text or a combination thereof;

c. Receiving a solution to said linguistic task by the subject through the computer; and d. If said solution is not correct, providing one or more additional linguistic clues to the subject, said one or more additional linguistic clues comprising content capable of activating concepts related to said one or more words but wherein i) said content does not include said one or more words or synonyms thereof, or ii) if said content does include said one or more words or synonyms thereof, said content does not comprise written text.

Optionally said providing one or more words by the subject comprises entering said one or more words to the computer.

Optionally said providing one or more words by the subject comprises identifying said one or more words by the subject.

Optionally said one or more linguistic clues in stages b or d comprises a plurality of clues and wherein said plurality of clues is revealed sequentially.

Optionally each clue is revealed separately, such that only one clue is revealed at a given time.

Optionally said providing one or more linguistic clues to the subject further comprises penalizing the subject if the subject requests display of a previously displayed clue.

Optionally said one or more linguistic clues comprises a plurality of clues and wherein said plurality of clues is revealed simultaneously.

Optionally said sequence is selected according to a requirement for integration of said plurality of linguistic clues by the subject.

Optionally said receiving said solution comprises analyzing said solution and wherein said analyzing said solution further comprises analyzing a correctness of said solution and one or more of a time required to complete said solution, a number of clues provided to the subject before said solution is submitted, a number of guesses before the correct solution was submitted, a number of times previously seen clues were displayed again, or a combination thereof.

Optionally the method comprises repeating stages a-d at least once.

Optionally at least one of said linguistic task, said one or more linguistic clues, the specific instructions or the scoring system upon repetition of stages a-d is different.

Optionally said providing said plurality of linguistic clues to the subject, through the display of the computer, further comprises selecting said linguistic clues such that the subject integrates said plurality of linguistic clues to solve said linguistic task.

Optionally said providing said plurality of linguistic clues to the subject, through the display of the computer, further comprises selecting said linguistic clues according to a level of difficulty.

Optionally said level of difficulty is determined according to a semantic ability of the subject.

Optionally said providing said plurality of linguistic clues to the subject, through the display of the computer, further comprises selecting said linguistic clues according to a semantic ability of the subject to be improved.

Optionally the method further comprises determining a semantic ability of the subject according to a diagnostic test.

Optionally a type of said diagnostic test is identical to a type of said previously performed diagnostic test.

Optionally said diagnostic test is identical to said previously performed diagnostic test but with different content.

Optionally a type of said diagnostic test is different from a type of said previously performed diagnostic test.

Optionally said diagnostic test comprises performing the method of stages a-d at least once.

Optionally said diagnostic test comprises performing a different diagnostic test other than the method of stages a-d.

Optionally said selecting said linguistic clues further comprises selecting a game world for the subject, said game world having a plurality of characteristic features, including at least one or more of instructions, incentives, type of clues, penalty on display of previous clues, sequence of clues and time of exposure of a given clue; and selecting said linguistic clues also according to said game world.

Optionally the method further comprises providing an incentive to the subject to provide said solution through the computer.

Optionally said incentive comprises one or more of points to obtain a reward, points convertible to monetary value, points relating to progress and/or points for comparison between different users.

According to at least some embodiments of the present invention, there is provided a method for improving a semantic ability of a subject, the method being performed by a computer, the method comprising:

a. Analyzing a semantic ability of the subject through the computer according to a diagnostic test;

b. Displaying a linguistic task to the subject on a display of the computer, said linguistic task comprising providing one or more words;

c. Providing one or more linguistic clues to the subject, through the display of the computer, said one or more linguistic clues comprising content capable of activating concepts related to said one or more words but i) said content does not include said one or more words or synonyms thereof, or ii) if said content does include said one or more words or synonyms thereof, said content does not comprise written text, wherein said linguistic clue comprises an image, audio, video, text or a combination thereof;

d. Receiving a solution to said linguistic task by the subject through the computer;

e. If said solution is not correct, providing one or more additional linguistic clues to the subject, said one or more additional linguistic clues comprising content capable of activating concepts related to said one or more words but wherein i) said content does not include said one or more words or synonyms thereof, or ii) if said content does include said one or more words or synonyms thereof, said content does not comprise written text;

f. Repeating stages b-e at least once.

Optionally the method further comprises in stage f analyzing said semantic ability of the subject through the computer according to a diagnostic test, to determine whether an improvement in said semantic ability of the subject has occurred.

Optionally a type of said diagnostic test is identical to a type of said diagnostic test of stage a.

Optionally said diagnostic test is identical to said diagnostic test of stage a but with different content.

Optionally a type of said diagnostic test is different from a type of said diagnostic test of stage a.

Optionally the method further comprises in stage g, repeating stages b-e at least once and altering at least one of said linguistic task, said one or more linguistic clues, the specific instructions, the scoring system or a level of difficulty thereof according to said diagnostic test of stage f.

Optionally said providing one or more words by the subject comprises entering said one or more words to the computer.

Optionally said providing one or more words by the subject comprises identifying said one or more words by the subject.

Optionally said one or more linguistic clues in stages b or d comprises a plurality of clues and wherein said plurality of clues is revealed sequentially.

Optionally each clue is revealed separately, such that only one clue is revealed at a given time.

Optionally said providing one or more linguistic clues to the subject further comprises penalizing the subject if the subject requests display of a previously displayed clue.

Optionally said one or more linguistic clues comprises a plurality of clues and wherein said plurality of clues is revealed simultaneously.

Optionally said sequence is selected according to a requirement for integration of said plurality of linguistic clues by the subject.

Optionally said receiving said solution comprises analyzing said solution and wherein said analyzing said solution further comprises analyzing a correctness of said solution and one or more of a time required to complete said solution, a number of clues provided to the subject before said solution is submitted, a number of times previously displayed clues were displayed again and a combination thereof.

Optionally said selecting said linguistic clues further comprises selecting a game world for the subject, said game world having a plurality of characteristic features, wherein at least one of said linguistic task, said one or more linguistic clues, the specific instructions or the scoring system upon repetition of stages a-d is different; and selecting said linguistic clues also according to said game world.

Optionally the method further comprises providing an incentive to the subject to provide said solution through the computer.

Optionally said incentive comprises one or more of points to obtain a reward, points convertible to monetary value, points relating to progress and/or points for comparison between different users.

Optionally said providing said plurality of linguistic clues to the subject, through the display of the computer, further comprises selecting said linguistic clues such that the subject integrates said plurality of linguistic clues to solve said linguistic task.

Optionally said providing said plurality of linguistic clues to the subject, through the display of the computer, further comprises selecting said linguistic clues according to a level of difficulty.

Optionally said level of difficulty is determined according to a semantic ability of the subject.

Optionally said providing said plurality of linguistic clues to the subject, through the display of the computer, further comprises selecting said linguistic clues according to a semantic ability of the subject to be improved.

According to at least some embodiments of the present invention, there is provided a method for determining semantic ability of a subject, the method being performed by a computer, the method comprising:

a. Displaying a linguistic task to the subject on a display of the computer, said linguistic task comprising providing one or more words by the subject to the computer;

b. Providing one or more linguistic clues to the subject, through the display of the computer, said one or more linguistic clues comprising content capable of activating concepts related to said one or more words but wherein said content does not include said one or more words or synonyms thereof, wherein said linguistic clue comprises an image, audio, video, text or a combination thereof;

c. Receiving a solution to said linguistic task by the subject through the computer, said solution comprising providing one or more words by the subject through the computer, the subject integrates said plurality of linguistic clues to solve said linguistic task; and d. Analyzing said solution to determine the semantic ability of the subject.

Optionally said providing said one or more linguistic clues comprises displaying a plurality of linguistic clues simultaneously to the subject through said display.

Optionally said providing said one or more linguistic clues comprises displaying said plurality of linguistic clues sequentially to the subject through said display in a sequence, wherein said sequence is selected according to a requirement for integration of said plurality of linguistic clues by the subject and/or according to a selection by the subject.

Optionally each linguistic clue is displayed singly in said sequence such that said plurality of linguistic clues is not displayed simultaneously, wherein optionally the subject selects the clue.

Optionally stages a-d are repeated at least once, optionally with one or more differences.

According to at least some embodiments of the present invention, there is provided a method for improving a semantic ability of a subject having a compromised semantic ability, the method being performed by a computer, the method comprising:

a. Analyzing the compromised semantic ability of the subject through the computer according to a diagnostic test;

b. Displaying a linguistic task to the subject on a display of the computer, said linguistic task comprising providing one or more words, said linguistic task being selected according to a result of said diagnostic test;

c. Providing one or more linguistic clues to the subject, through the display of the computer, said one or more linguistic clues comprising content capable of activating concepts related to said one or more words but i) said content does not include said one or more words or synonyms thereof, or ii) if said content does include said one or more words or synonyms thereof, said content does not comprise written text, wherein said linguistic clue comprises an image, audio, video, text or a combination thereof, the subject integrates said plurality of linguistic clues to solve said linguistic task;

d. Receiving a solution to said linguistic task by the subject through the computer;

e. If said solution is not correct, providing one or more additional linguistic clues to the subject, said one or more additional linguistic clues comprising content capable of activating concepts related to said one or more words but wherein i) said content does not include said one or more words or synonyms thereof, or ii) if said content does include said one or more words or synonyms thereof, said content does not comprise written text;

f. Repeating stages b-e at least once.

Optionally the method further comprises analyzing said semantic ability of the subject through the computer according to a diagnostic test, wherein said diagnostic test is identical or different from said diagnostic test of stage a, to determine whether an improvement in said compromised semantic ability of the subject has occurred.

Optionally said providing one or more linguistic clues to the subject further comprises selecting said one or more linguistic clues according to said result of said diagnostic test.

Optionally a level of difficulty of stages b-e is selected according to said result of said diagnostic test.

Optionally a level of difficulty of stages b-e is selected according to a result of previously performing stages b-e by the subject.

Unless otherwise defined, all technical and scientific terms used herein have the same meaning as commonly understood by one of ordinary skill in the art to which this invention belongs. The materials, methods, and examples provided herein are illustrative only and not intended to be limiting.

Implementation of the method and system of the present invention involves performing or completing certain selected tasks or stages manually, automatically, or a combination thereof. Moreover, according to actual instrumentation and equipment of preferred embodiments of the method and system of the present invention, several selected stages could be implemented by hardware or by software on any operating system of any firmware or a combination thereof. For example, as hardware, selected stages of the invention could be implemented as a chip or a circuit. As software, selected stages of the invention could be implemented as a plurality of software instructions being executed by a computer using any suitable operating system. In any case, selected stages of the method and system of the invention could be described as being performed by a data processor, such as a computing platform for executing a plurality of instructions.

Although the present invention is described with regard to a "computer" on a "computer network", it should be noted that optionally any device featuring a data processor and/or the ability to execute one or more instructions may be described as a computer, including but not limited to a PC (personal computer), a server, a minicomputer, a cellular telephone, a mobile device, a PDA (personal data assistant), a tablet or the like. Any two or more of such devices in communication with each other, and/or any computer in communication with any other computer may optionally comprise a "computer network".

Optionally a computer network may comprise a wired communication network, including but not limited to a PSTN (public switched telephone network) and/or other wired telephone and/or circuit-switched network, an optical communication network, a fiber-optic communication network and the like or RF network, and/or any combination of the aforesaid networks, which may optionally be private or public networks; and a wireless data network including but not limited to a cellular network, a WiMAX network, an EV-DO network, an RTT network, a Flash-OFDM network, an iBurst network, a HSPA network, an EDGE network, a GPRS network, a GPS satellite network, a Wi-Fi network, a UTMS network, and/or any combination of the aforesaid networks, which may optionally be private or public networks. Combinations of wired and wireless networks may also optionally be employed.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in order to provide what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIGS. 7A-7C relate to exemplary screenshots according to at least some embodiments of the present invention;

FIGS. 9-23 and 24A-24C show data obtained by testing a system and method according to at least some embodiments of the present invention on a group of individuals.

DETAILED DESCRIPTION OF AT LEAST SOME EMBODIMENTS

Figure 1A:
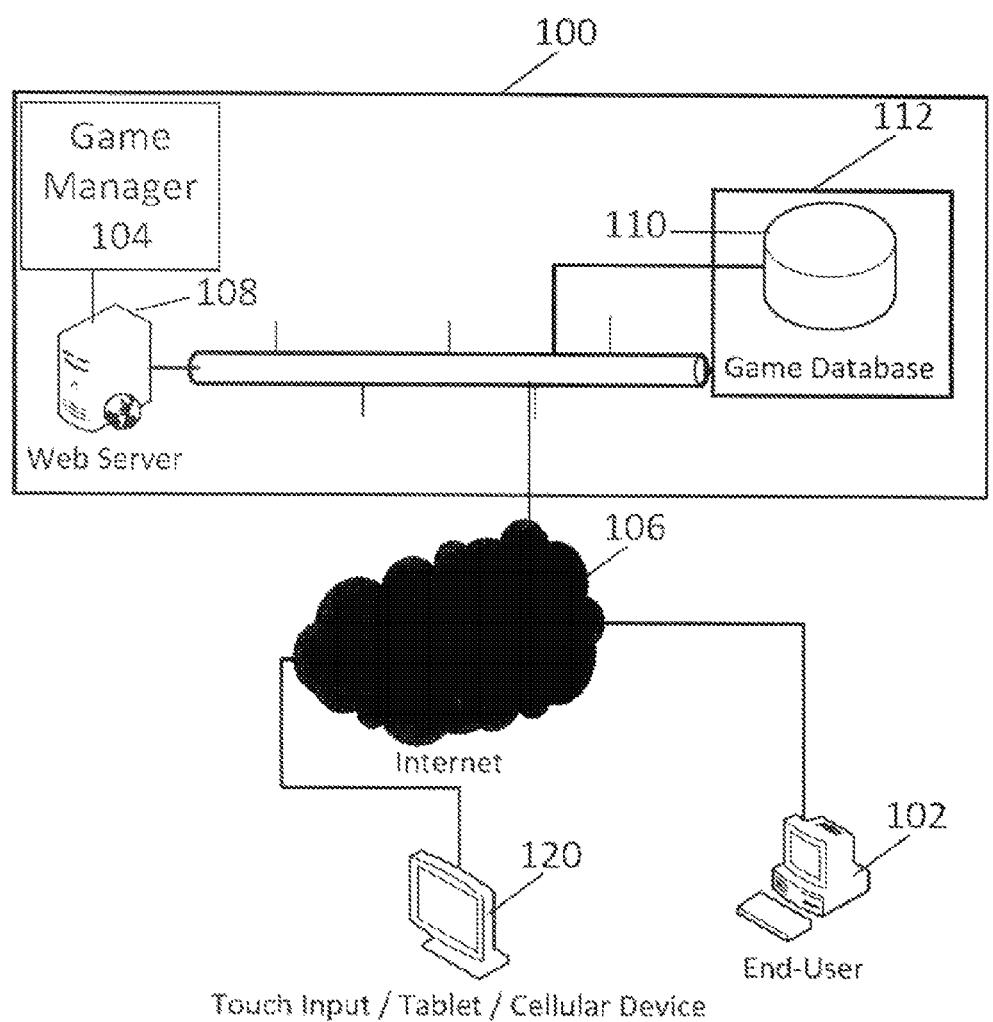
FIGS. 1A and 1B show different embodiments of a system according to the present invention.
Figure 1B:
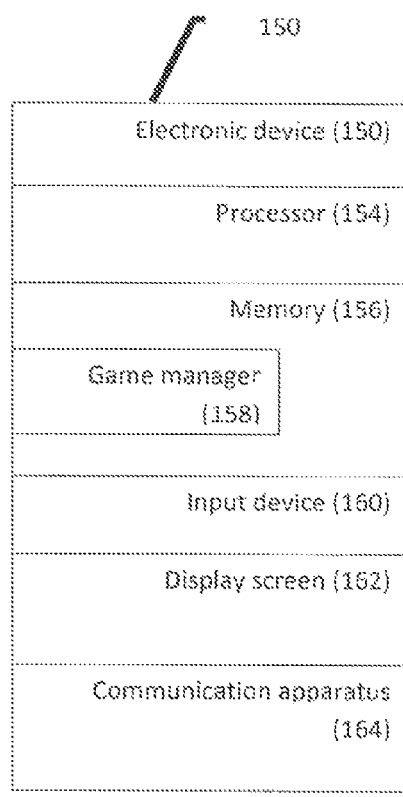

Turning now to the drawings, FIG. 1 shows two exemplary, illustrative non-limiting configurations of a system according to some embodiments of the present invention. FIG. 1A shows a system featuring a server and client, while FIG. 1B shows an electronic device operating stand-alone software. For these non-limiting examples, the linguistic tasks are described as being performed through a game, but the present invention is not limited to such a performance.

Turning to FIG. 1A, as shown, a system 100 features an end user computer 102 for enabling the user to perform the linguistic tasks to reach a solution as part of operating a game. End user computer may optionally feature an input device 120, which may also optionally be able to communicate separately as shown. End user computer 102 communicates with a game manager 104, for managing the game and for optionally providing at least part of the game functionality, through a computer network 106, which for example may optionally be implemented as the Internet. For example and without limitation, game manager 104 may optionally set linguistic tasks, select levels of difficulty, optionally perform one or more pre or post diagnostic tests and so forth.

End user computer 102 may optionally have software installed on it (not shown) and/or may rely upon game manager 104 for supplying the game functionality. For this example, a significant amount of the game functionality (if not all of it) is provided through game manager 104. Game manager 104 at least performs the following functions: managing the inquiries of the user during a stage, allowing navigation between stages, determining the level of difficulty at each stage (for example, determining the rules of the game and/or the clues to be supplied) and also building and providing the clues themselves. Game manager 104 also preferably determines whether a solution is correct and keeps score (or otherwise assesses the interactions of the user with the game). Game manager 104 also supports game-related customizations, for example optionally including but not limited to providing performance based feedback and adapting training program (including number of training sessions, composition of each session (frequency of different game worlds), content of each stage and level of difficulty).

Figure 2:
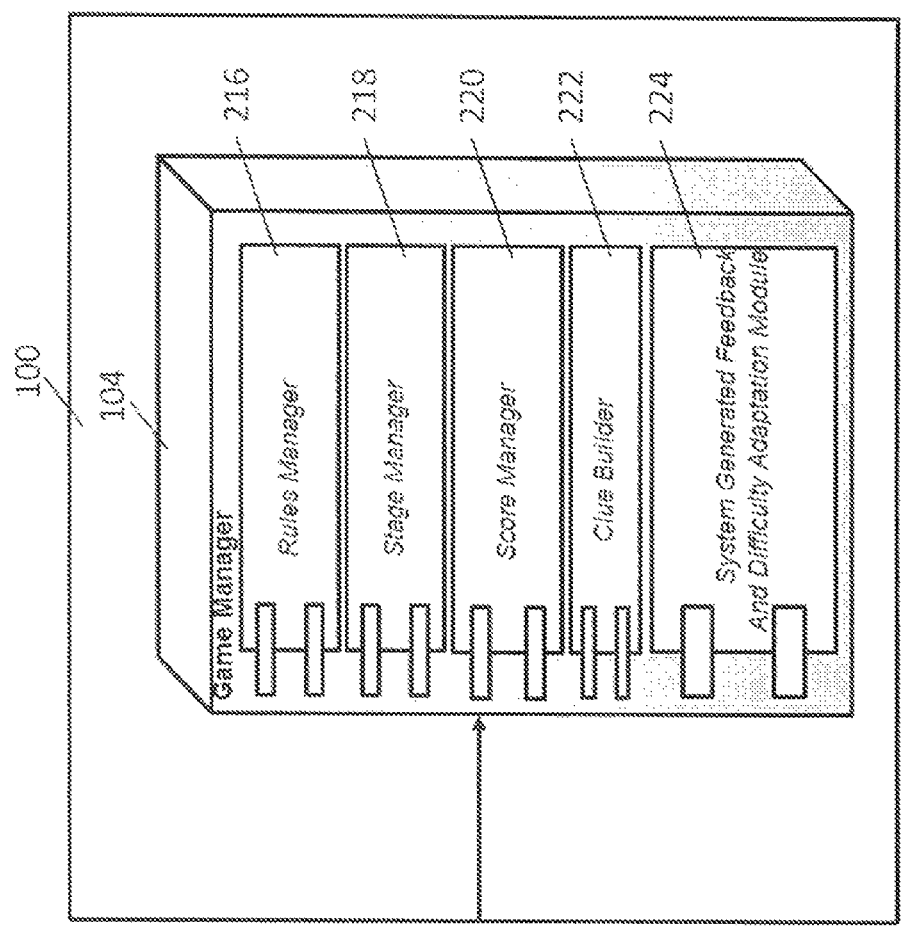
FIG. 2 shows a more detailed diagram of a system according to FIG. 1A.

Optionally a game manager may also be present at end user computer 102 (not shown; see FIGS. 1A and 2).

Optionally, the user may interact with the game through a web browser (not shown), such that the game functionality may be provided through a plug-in or other connective software. Implementation through a web browser also optionally enables the software to have a "zero footprint" and hence to not be installed permanently on end user computer 102.

To assist with embodiments in which game manager 104 may optionally provide at least some of the game functionality, system 100 may optionally feature a web server 108, for example for enabling at least some of the game functionality to be provided through a web browser on end user computer 102, with or without such installed software as plug-ins and the link.

Linguistic tasks (particularly components required to perform such tasks), information about levels of difficulty, diagnostic tests and so forth may optionally be stored on a game database 110, operated by a game database server 112 as shown. For example and without limitation, game database 110 may optionally store user performance history (including all of the actions that the user performs with regard to end user computer 102, even not related to the game—such as viewing reports and graphs etc.—in order to improve the user's experience with the game). Game database 110 also stores the clues and clue components, for example including but not limited to media files such as images and sound files (alternatively these items may be stored at web server 108 (not shown)). Game database 110 also stores general information about the user, various characteristics and definitions for the game (including but not limited to game rules, game appearance, including game "skins", different levels of each game), various system parameters and user groups, and/or may also optionally store one or more of results of diagnostic tests (whether they were carried within the system or externally); logs and tracks progress measures beyond score (time, number of guesses, number of clues accessed—per stage) and also optionally training programs and feedback content.

FIG. 1B shows another optional, exemplary embodiment according to the present invention, in which a system 150 features an electronic device 152 operating stand-alone software, shown as a game manager 158. Electronic device 152 may optionally be any type of computer as described herein and/or may optionally be a special purpose device designed to implement the game.

As shown, electronic device 152 features a processor 154 for performing one or more computations and hence for supporting operation of game manager 158. Electronic device 152 also features memory 156 for storing information, preferably permanently, which includes such data as required for operation of the game, for example optionally including the various types of data stored in game database 110 of FIG. 1A.

In system 150, game manager 158 optionally performs at least the following local functions, even if not operating as a stand-alone software: controlling security and usability, rule enforcement and managing user interactions with the game. For example, game manager 158 may optionally and preferably determine whether one or more solutions of the user are correct, and may also optionally "keep score" (for a game implementation). Game manager 158 optionally and preferably also controls security, for example to prevent hacking of the game. Usability may optionally relate to determining the difficulty of clues, the order in which they are presented, how they are displayed on electronic device 152, how the user may enter solutions or request more information (for example to request further clues to be displayed). Rule enforcement may optionally relate to game rules, for example preventing the user from viewing more than one clue at a time (if this is a rule of the game). Game manager 158 may also optionally determine penalties according to the game rules; for example, if the user wishes to reveal a clue that was already revealed, then a penalty of point deduction from the user's score is assessed. Game manager 158 also preferably assists with timing the user if that is important for game assessment; for example, measuring the length of time required for the user to enter any solution or a correct solution, or the timing between clue requests and so forth.

However, game manager 158 may also optionally operate as a completely "stand alone" module, in which case game manager 158 preferably incorporates further functionality from the game manager located at the server for FIGS. 1A and 2.

Electronic device 152 also features an input device 160, such as a keyboard, mouse, joystick or other pointing device, for receiving commands from the user. Such an input device 160 may optionally be implemented with end user computer 102 of FIG. 1A (not shown).

Electronic device 152 may optionally feature a display screen 162 for displaying one or more linguistic tasks, clues, information displayed to the user or entered by the user, and so forth. Optionally display screen 162 may be combined with input device 160 in the form of a touch screen (not shown) which again may optionally be implemented with end user computer 102 of FIG. 1A.

Electronic device 152 may also optionally feature a communication apparatus 164, for communicating with external computers and/or databases (not shown), for example to obtain more information, linguistic tasks, clues and so forth.

FIG. 2 shows system 100 with additional details regarding various components of each entity. As shown, user computer 102 features a web browser 200, comprising a UI manager 202 and a business logic software 204. Business logic software 204 comprises a game manager 206 and an AJAX client 208. AJAX client 208 may optionally be implemented through other types of technologies, but preferably is implemented through a technology that supports similar asynchronous data retrieval from web server 108 as shown.

Business logic software 204 preferably manages the overall aspects of the game that are controlled from end user computer 102, which are optionally and preferably more local in nature, as described with regard to the operation of game manager 206 below. Alternatively, business logic software 204 may optionally manage more aspects of the game if "local" is defined more broadly, or fewer aspects of the game if "local" is defined more narrowly.

Optionally, business logic software 204 may be separate from web browser 200; combining it with web browser 200 may optionally be implemented for browser plug-ins and other similar software configurations. Also AJAX client 208 may optionally be separate from business logic software 204 or otherwise separate from game manager 206; for example, AJAX client 208 may optionally be implemented at UI manager 202. In addition, AJAX client 208 does not need to be an AJAX client; other types of client support software are also contemplated within the present invention. AJAX client 208 does preferably support client-side interactions (that is, at end user computer 102) with the server (that is, web server 108, which also may optionally be implemented as any suitable type of server that can interact with the client at end user computer 102).

UI manager 202 preferably handles the direct display aspects of the user interface displayed by end user computer 102, in conjunction with functionality supplied by AJAX client 208. In addition, UI manager 202 preferably supports interactions of the user with end user computer 102, for example with an input device, such as a keyboard or pointing device.

Game manager 206 preferably operates as described with regard to the game manager of FIG. 1A, at least with regard to those functions described as being local in nature. For example, game manager 206 preferably controls security and usability, performs rule enforcement and manages user interactions with the game. For example, game manager 206 may optionally and preferably determine whether one or more solutions of the user are correct (alternatively this may be determined at game manager 104), and may also optionally "keep score" (for a game implementation). Game manager 206 optionally and preferably also controls security, for example to prevent hacking of the game. Usability may optionally relate to determining how clues are displayed on end user computer 102, how the user may enter solutions or request more information (for example to request further clues to be displayed). Rule enforcement may optionally relate to game rules, for example preventing the user from viewing more than one clue at a time (if this is a rule of the game). Game manager 206 may also optionally determine penalties according to the game rules; for example, if the user wishes to reveal a clue that was already revealed, then a penalty of point deduction from the user's score is assessed. Game manager 206 also preferably assists with timing the user if that is important for game assessment; for example, measuring the length of time required for the user to enter any solution or a correct solution, or the timing between clue requests and so forth. However, such information as the game world implementation and the clues themselves are preferably downloaded from web server 108.

As shown web browser 200 retrieves data, through computer network 106 as previously described, from web server 108, which may optionally be configured as shown. In this configuration, web server 108 preferably comprises one or more web service technologies, such as (for example and without limitation), a web server 210 (shown as an Apache web server for illustration only) and PHP web service 212. Different types of technologies could optionally be used in place of this combination, optionally including any suitable web server technology and other supportive technologies such as Ruby on Rails, Python and the like. However, such technologies are preferably able to interact with the client at end user computer 102.

Web server 108 also preferably features a business logic software 214, comprising a user sessions manager 216 and a game manager 218. As for business logic 204 of end user computer 102, business logic 214 manages those aspects of the game that are implemented at web server 108, for example as described with regard to game manager 104 below.

Business logic 214 manages any aspects of the game that are not managed through business logic 204; therefore, the greater the role of business logic 204, the lesser the role of business logic 214 and vice versa. Business logic 214 at least needs to handle those aspects of the game that are managed at web server 108.

Business logic 214 is in communication with game manager 104 through a game manager interface 226. However, if game manager 104 is operated by web server 108, game manager 104 may optionally be incorporated with business logic 214 as shown.

Game manager 104 preferably comprises a rules manager 216 for managing the rules, including without limitation determining the rules, selecting rules according to a level of difficulty and/or game implementation, and so forth. Rules manager 216 is optionally operated as a rules engine, in which inquiries are dynamically processed to determine a dynamic output, or may alternatively operate more as a look-up apparatus.

Game manager 104 also preferably comprises a stage manager 218 for determining the level of difficulty experienced by the user. Stage manager 218 preferably provides input regarding this level of difficulty to rules manager 216, so that the correct rules are selected for any particular stage of the game. The stages themselves are optionally also managed through business logic 214, through a user sessions manager 228, which keeps track of user interactions with the game, including but not limited to "how well" the user is performing with regard to the game. "How well" the user is doing is optionally determined according to one or more of the score of the user and/or timing of the user as described above, and so forth—preferably as determined by the rules of the game through rules manager 216. Other optional parameters include number of clues accessed or re-opened; and the number of incorrect guesses (solutions).

Stage manager 218 and user sessions manager 228 both optionally and preferably receive input from a score manager 220, which determines "how well" the user is performing the game as described above. Stage manager 218 may also optionally choose the next level which may alternatively be pre-determined by the system administrator.

A clue builder 222 preferably builds the clues, according to input from rules manager 216, from various clue components which may optionally include one or more images, audio files, video files, text files and the like. Clue builder 222 preferably has a rules interpreter (not shown) for interpreting the rules to build the clues; alternatively, such as rules interpreter may be located at rules manager 216 (not shown). Clue builder 222 may also optionally use pre-defined clue templates that can be edited any time by the system administrator to allow skinning; that is, changing the structure of the presented clue and/or its appearance.

A system generated feedback and difficulty adaptation module 224 preferably supplies feedback to rules manager 216 and also optionally to clue builder 222 and/or stage manager 218, according to information received from user sessions manager 228 and/or stage manager 218 and/or score manager 220, or some combination of these entities (for example, optionally and preferably information is received both from user sessions manager 228 and score manager 220).

Figure 3:
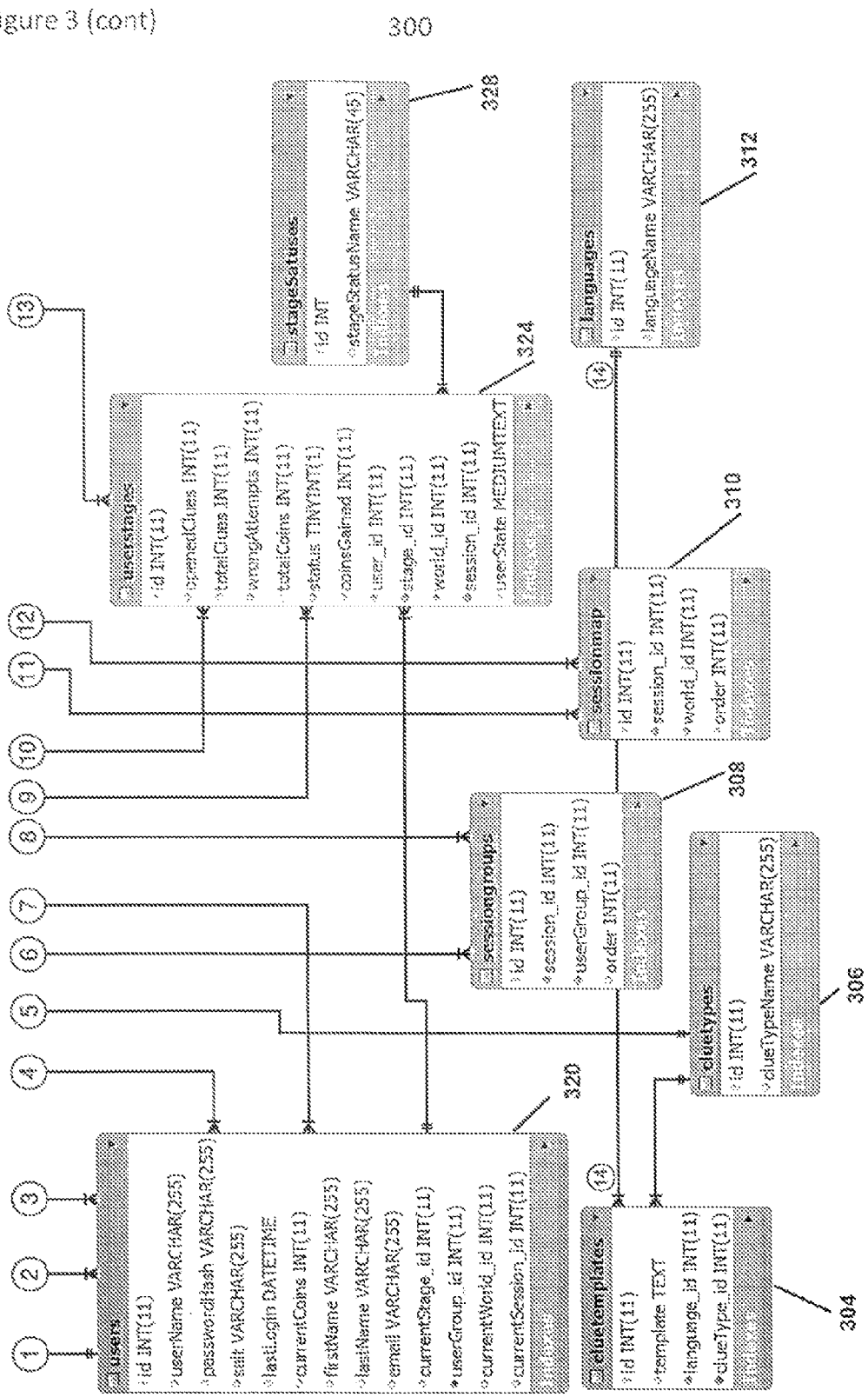
FIG. 3 shows an ERD diagram of the software according to at least some embodiments of the present invention.

FIG. 3 shows an exemplary, non-limiting, illustrative entity relationship model (ERD) with regard to the operation of game manager 104. An ERD 300 is provided for the purpose of illustration only, as many different software constructions and implementations are possible and contemplated within the scope of the present invention.

As shown, ERD 300 comprises a clues table 302, which is a table used for storing information about the clues such as their type (sound, image, video, text etc.), whether they can be re-opened (that is displayed more than once to the user) and/or whether they have a special game function (for example, acting as a rescue wheel as described in greater detail below). Clues can also be interactive and require the user to answer a question, in which case a text box will be attached to the clue presentation layout and the correct answer will be stored in the metadata column. In addition, clues may have scores, for example for a penalty on reopening the clue or a prize for providing a correct answer for interactive clues.

Clues table 302 is in communication with a stages table 326. Stages table 326 is a table used to define the different stages. Each stage is linked with a world using the world property. The table also contains global information about the stages such as the solution to the stage and rules enforcement definitions (such as enforcing clue opening order).

Stages table 326 is in turn in contact with a worlds table 318. A world is a pre-defined set of stages (each stage is a linguistic task with one solution). The worlds table 318 is used to define global information about the worlds (including but not limited to world name, global rules overrides, etc.).

Worlds table 318 is in contact with a user worlds table 316, which is in turn in contact with a users table 320 and a sessions table 314. User worlds table 316 is a table used to describe a user's performance within the worlds (a summary, such as number of stages completed etc.).

Users table 320 is a table containing general information about the user, such as their encrypted password, last login time, name; the table also links each user to a specified group in a usergroups table 322. Usergroups table 322 is a table containing definitions of each group. Each user has to be assigned to a group (using the users table 320). Each group is than assigned to a certain path built out of a specific set of worlds defined customized specifically for that group. For example and without limitation, different groups could relate to the speed with which the level of difficulty increases, the initial level of difficulty, specific semantic abilities which are to be trained or otherwise improved, and so forth.

A session is a set of worlds and/or different levels of difficulty of the game or any other divisions therefore within a single performance of the game by the user. Session table 314 is used for basic definition of the sessions that exists in the system (mainly the session name).

Users table 320 is also in contact with user stages table 324 as previously described, which is in turn in contact with a stage statuses table 328, which relates to the status of each stage.

A cluetemplates table 304 is a table used for defining the presentation layout of each of the clue types. Each clue type and language combination has a different layout. The layout is specified inside the template column using code that is compatible with the user interface technology on the end user computer, such as (for example and without limitation) HTML and JavaScript.

A clueTypes table 306 is a table used as a helper map for defining the types of clues that exists in the system (again—image, sound, video, text etc.). ClueTypes table 306 is in contact with cluetemplates table 304 and clues table 302. Clues table 302 is in contact with cluetemplates table 304, which in turn is in communication with cluetypes table 306.

Sessiongroups table 308 is a table used for mapping sessions to user groups. Each user group will go through numerous sessions each containing numerous worlds (each containing numerous levels). The table is also used to define a rule to enforce between each session (such as usage limit, where a user needs to wait x hours before the user is permitted to attempt the next session, upon completing the previous one).

Sessiongroups table 308 is also in contact with session table 314 and usergroups table 322.

A sessionmap table 310 is a table used for mapping numerous worlds to each session, for specifying which worlds each session will include and order in which the worlds are navigated.

Sessionmap table 310 is in contact with sessions table 314 and worlds table 318.

Userstages table 324 is a table containing the performance information for every stage the user attempted to solve, including information such as the current score, the result of the level (user can either solve of skip) and total clues that were opened.

Figure 4:
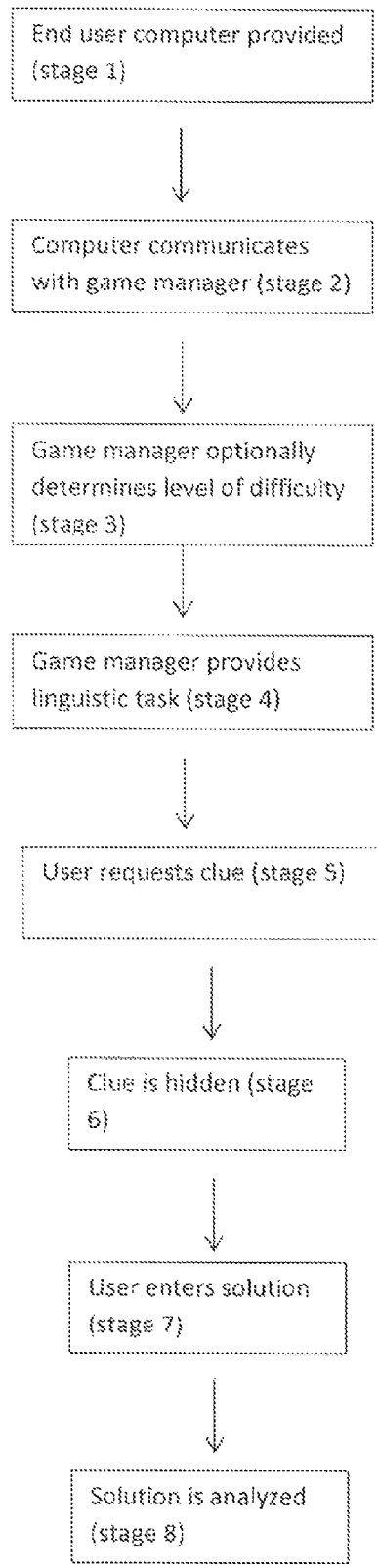
FIG. 4 shows a method according to at least some embodiments of the present invention.

FIG. 4 is a diagram of an illustrative, non-limiting method of at least some embodiments for performing a game as described herein for training the semantic ability of a subject (user as described herein), for example in FIGS. 1-3. However, the below method is not limited to implementation with the system of any of FIGS. 1-3 and may optionally be implemented differently. Furthermore, for this non-limiting example of a game, the following structure is discussed for the sake of clarity only. Within the game, each session is composed of a plurality of worlds. Each world is composed of a plurality of stages. Each stage has one task, one solution and a plurality of clues.

As shown, in stage 1 an electronic device is provided to the user, which in this example is an end user computer, for example as shown in FIG. 1A and FIG. 2. If the electronic device is standalone, then most, if not all, of the functionality will be performed by the electronic device and will not be shared with a server, as in this exemplary method.

In stage 2, the end user computer communicates with a game manager, for example through a web server as described with regard to FIGS. 1A and 2. In stage 3, the game manager optionally determines a level of difficulty that the user should encounter in the game itself. Stage 3 may optionally be performed periodically throughout the game.

In stage 4, the game manager provides a linguistic task to the user through the end user computer, in which the linguistic task requires the user to provide one or more words to the game manager through the end user computer, whether by entering the words (for example through the keyboard), selecting the words from a list and so forth. The task is optionally and preferably selected according to the previously determined level of difficulty.

In stage 5, the user may optionally provide a solution directly, but would typically be expected to request the provision of one or more linguistic clues to determine the solution (that is, the words to provide through the end user computer). Such one or more linguistic clues comprise content capable of activating concepts related to said one or more words. However, such content does not include said one or more words or synonyms thereof. The linguistic clue optionally comprises an image, audio, video, text or a combination thereof, each unit of which is referred to as a "linguistic clue component" above. The linguistic clue is also optionally and preferably selected according to the above described level of difficulty.

Optionally and preferably, the user is not able to provide a solution (or "guess"), without viewing a plurality of clues, so that integration occurs.

Optionally and preferably, such content does not include one or more words or synonyms thereof as described above, but also optionally, if the content does include the one or more words or synonyms thereof, the content does not comprise written text.

Optionally, if a plurality of linguistic clues is provided, the clues are provided simultaneously. Optionally and preferably, if a plurality of linguistic clues is provided, the clues are provided sequentially. By "sequentially" it is meant singly (that is, each clue is provided separately) or alternatively, that more than one clue may be provided at once but still not all clues are displayed simultaneously. The order may optionally be chosen by the user or by the software (system). Also optionally the plurality of linguistic clues may be selected such that the user integrates the plurality of linguistic clues to solve the linguistic task as noted previously.

Optionally the user may be requested to complete a task within a clue (reading a text passage for example).

Optionally, there is some type of limit on the length of time that a user can view a linguistic clue, such that in stage 6, the clue is concealed from further viewing by the user. The user may optionally also be prevented from seeing another clue until a minimum period of time has elapsed. Optionally the user may be able to request to see the clue again, for example with a penalty according to the rules of the game.

Stages 4-6 may optionally be performed more than once, but preferably scoring of the game is at least partially determined according to such factors as the number of incorrect solutions to the task, time taken to find the correct solution, number of clues viewed once, number of clues viewed more than once and so forth.

In stage 7, the user enters a solution to the end user computer. In stage 8, the solution is analyzed by the end user computer and/or by the game manager to determine the semantic ability of the subject, for example according to the above parameters.

Again, stages 4-8 are optionally performed more than once, for example to facilitate playing a complete game by the user, in which a game comprises more than one level, or additionally or alternatively may optionally comprise more than one game world. In this embodiment, different game worlds may optionally relate to the emphasis change protocol as is known in the art training non-linguistic skills, but which has never been implemented for training linguistic skills (semantic abilities). Some non-limiting examples of such game worlds include:

1. Baseline—in this world, there are no special emphasis or rules. Participants are required to perform the basic task—open (display) the clues and guess (provide) the solution; where the optimal behavior of using the least amount of clues and guesses is highly rewarded.
2. Simplified—this is a simplified version of the baseline world. This world places a reduced load on memory capabilities, by permitting repeated access to clues at no cost. This world was used for on boarding the participants and allowing them to explore the game rules in a low demanding environment; and was presented at later stages to allow participants to explore different strategies for solving the basic task when the memory load is lower.
3. high-memory load—in this world, participants had to perform the basic task, with one constraint—re-opening a clue had a high cost. This manipulation was intended to guide participants to use their working memory more proficiently while performing the semantic exercise.
4. Deep dive—in this world, participants had to perform the basic task, with one constraint—they had to spend more time on selected clues. This manipulation was intended to guide participants to explore strategies that lean on deep elaboration of semantic networks around the presented concepts.
5. High-processing load—in this world, the clues' content, number and structure was manipulated such that the participants' cognitive resources' load was increased. Examples include longer passages, texts with frequently missing words, and more clues overall. This manipulation guided participants to explore less demanding strategies and adapt the use of existing strategies to ever more demanding contexts.
6. Context dependent—in this world, the clues' content and proximity was manipulated such that some clues provided essential context for interpretation of other clues or their relation to the solution word. For instance, two clues may optionally be provided that allude to the same phrase (that includes the solution word), each is associated to that phrase in a different way (e.g., solution word 'blood', clue 1: a text about unique siblings relationship, clue 2: a sentence about inherited qualities shared among relatives—both clues allude to 'blood relations'). This manipulation was intended to guide participants to explore strategies of semantic activation that are more context-dependent.
7. Literal and non-literal—in this world, clues' content was manipulated such that some clues referred to the solution word in a figurative way, and others—in a literal way. For instance, for the solution word 'bush', there would be clues referring to the literal meaning of 'beating around the bush' (e.g., an image of people beating something while standing around it) and others—to the figurative meaning (e.g., a quote of someone complaining that the conversation went on and on without hitting the painful matters). This manipulation was intended to practice participants in flexibility of activating and maintaining meanings that are related to a concept in different ways.
8. Ambiguous—in this world, the clues' content was manipulated such that selected clues were associated with each other in an ambiguous way—allowing more than one association between some of the clues. By introducing distractions, this manipulation demanded participants to inhibit possible associations in order to discover the one association that connects all clues. To allow that, participants were encouraged to read all clues (as opposed to the minimal number of clues). This manipulation practiced inhibitions of irrelevant concepts, an important subcomponent of successful semantic processing.
9. Filter the distractions—In this world, the rules has changed—one of the clues was not associated with the solution word. Participants were encouraged to open all clues and come up with a solution word that is associated to most clues, but not all of them. This manipulation practiced the skill of inhibiting irrelevant concepts.
10. Broad associations—in this world, the participants were encouraged to open all available clues (at no cost). This manipulation emphasized activation of a broad semantic network, as opposed to integrating remote associations based on the least possible number of clues.

Each game world preferably comprises different rules and may also optionally feature different linguistic tasks and/or clues (although optionally, one or more of tasks, clues or clue components is shared between the different worlds), and/or may optionally have different scoring systems. Each game world may also optionally have a different "skin" or visual appearance.

Figure 5:
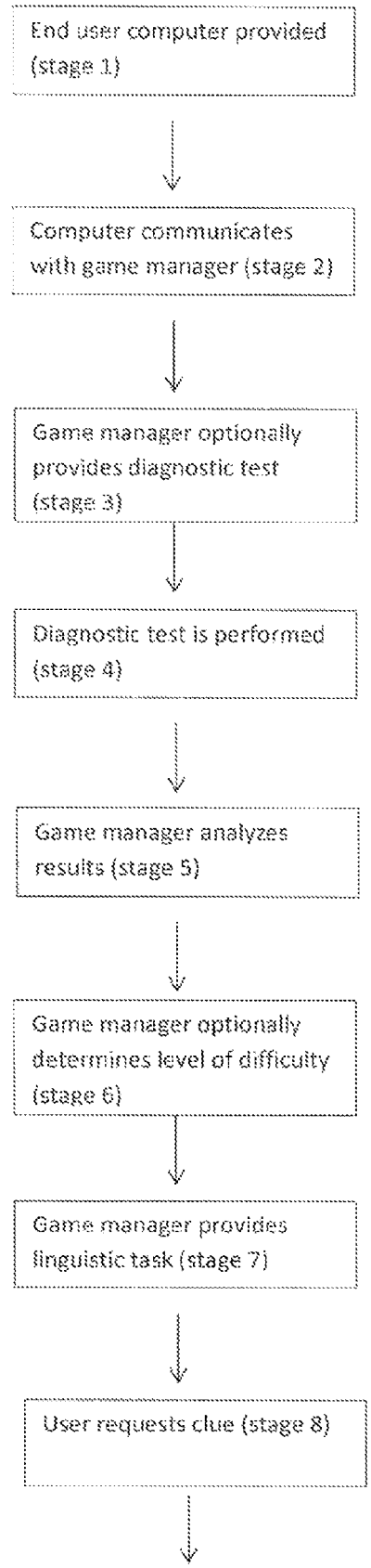
FIG. 5 shows a more detailed method according to at least some embodiments of the present invention.

FIG. 5 is a diagram of a more detailed, illustrative, non-limiting method of at least some embodiments for performing a game as described herein, for example in FIGS. 1-3. However, the below method is not limited to implementation with the system of any of FIGS. 1-3 and may optionally be implemented differently.

Stages 1 and 2 are performed as in FIG. 4. In stage 3, the game manager optionally provides a diagnostic test for the user to perform on the end user computer (alternatively, no such test is performed, a different test is performed and/or the game itself serves as a test). In stage 4, the diagnostic test is performed and in stage 5, the game manager (or alternatively another entity) analyses the results to determine a level of difficulty that the user should encounter in the game itself.

Stages 6-11 optionally correspond with stages 3-8 of FIG. 4; however, optionally various incentives are provided to the user for playing the game. For example, such incentives may optionally comprise (without limitation) points, positive messages, viewing of entertaining content (images, videos and/or text) or listening to an audio clip.

Stages 7-11 are optionally performed more than once. Also optionally, stages 5-11 are performed more than once. Stage 5 may optionally be performed periodically throughout the game.

In stage 12, another diagnostic test is optionally performed to see whether the user improved. As for the first diagnostic test in stage 3, optionally no such test is performed, a different test is performed and/or the game itself serves as a test. The diagnostic tests of stage 3 and 12 may optionally be the same or different, or may optionally be of the same or different type or category.

The method of either FIG. 4 or 5 may optionally be performed in the course of playing a game for many different populations of individuals, for example and without limitation for individuals seeking semantic language ability improvement (including but not limited to individuals seeking greater proficiency in their native language; translators; students about to be tested on language ability) and also for semantic language ability assessment, as well as for pedagogical methods for foreign languages or native languages. The assessment and/or treatment of abnormal semantic language ability, including both ability testing and improvement, are described with regard to FIG. 8 below.

Figure 6A:
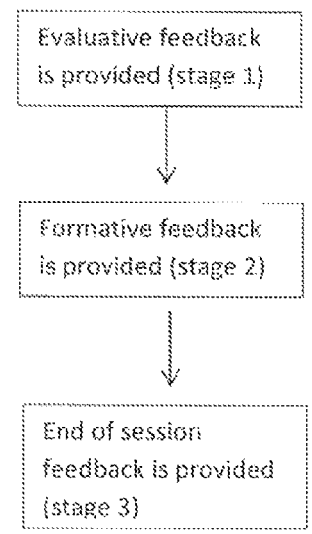
FIGS. 6A and 6B relate to illustrative, optional, non-limiting methods for further improvement according to at least some embodiments of the present invention.
Figure 6B:
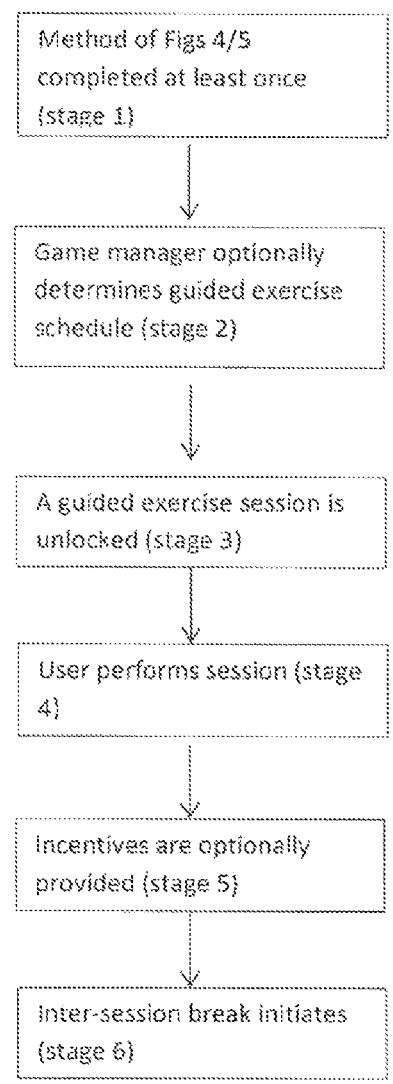

FIGS. 6A and 6B relate to illustrative, optional, non-limiting methods for further improvement according to at least some embodiments of the present invention. FIG. 6A relates to the optional provision of feedback while FIG. 6B relates to the optional provision of guided exercises. Either method may optionally feature training examples for normal individuals, foreign language translation and/or assistance in studying for aptitude tests. It should be noted that although this method is being described as a standalone method, the method is optionally and preferably performed with the methods of FIG. 4 or 5, such that FIG. 6A describe a process that optionally and preferably would occur during the processes describe in FIGS. 4 and 5, while FIG. 6B describes a process that will optionally occur after the processes described on FIG. 4 or 5 has occurred at least once (and preferably more than once).

FIG. 6A relates to the provision of feedback. An important component of the training method is formative feedback which is preferably provided intermittently—hence the potential requirement to interleave this method with the above described methods. This feedback is intended to create Knowledge of Results—enabling the trainees to understand not only their performance, but also its potential impact on their learning process and real-world goals. In the future, more data may be used to provide a comparison of the trainee's performance to norms and/of a personal baseline.

In stage 1, optionally evaluative feedback is provided continuously at various stages of the game. This feedback is intended to facilitate the game play and reinforce the reward scheme as incentive for desired behaviors in every point in the training. Such evaluative feedback optionally comprises input-based feedback: Immediate feedback is provided in reaction to all inputs from the participant (i.e. when responding on a clue/surprise, or guessing the solution). This feedback includes performance feedback (correct/incorrect) and number of points won/lost.

Optionally and additionally or alternatively, continuous feedback on game status is provided, in which at any given time point, participants could see on screen their current number of points and the unused clues.

In stage 2, optionally, once trainees complete all the levels of a game world, they are presented with elaborated formative feedback. The feedback includes:

Performance feedback (based on individual performance during that world)

Goal-directed feedback (including tips for improvement, as well as a reference between individual performance to the high-level training objectives of the specific world and their expression in real-life language processing For example, if the user is only able to solve half of the stages in a given world practicing use of the context, the feedback might be—"you have completed the 10th world of your training program, but you only found half of the solution words in this world. This world practiced skills of utilizing contextual information to solve the task—we use contextual information in every conversation to help us disambiguate concepts and form expectations on the new information that is about to be introduced. In the future, if you cannot find the solution word, try going back to the clues you have opened and see how they can be used as context to understanding each other".

In stage 3, optionally end of session feedback is provided. As noted above, each session comprises several levels or worlds; for the latter designation, each world may optionally comprise several levels. At the end of each session, optionally more goal oriented feedback is presented at the end of each session, reviewing the high-level training objectives covered during the session and feedback on number of points accumulated during the session.

For example, the feedback may state "the training session today included ever-more complicated clues, and the challenges are just piling up as you progress the training program. As clues' complexity increases, you practice new strategies to connect concepts, and practice the strategies that work for you in different settings. Continuing this practice will ensure that you can utilized this strategies in the right way in daily life! Take a couple of days of rest before tackling the next training session. Good luck!"

Optionally for any of the above stages, social feedback may be included to invoke motivation by cultivating a notion of competition. This may include information on performance of a single trainee in comparison to a tailored reference group (matched by age/baseline/existing social network etc.), but would focus on the individual progress and not absolute performance. It might be delivered in/out the application (perhaps interfacing with social media website such as Facebook; or on a leader board presented in a public location with social relevance).

FIG. 6B relates to a method for guided exercises, for example for maintenance sessions. Following the initial training (stage 1), different applications of the training method may include varying number of training sessions (each including a varying number of stages), and varied training schedules (including number of stages per session, and time between sessions). In addition, the programs may include core-sessions (performed in a given schedules), and a set of maintenance-sessions.

On stage 2, the guided exercise program is determined by the game manager or manually. Alternatively, it could be pre-set. The program includes maintenance sessions and may vary in number of sessions and their length, as well as time between sessions. The program might be determined by (1) a default in the specific application; (2) system recommendation based on the individual performance and prior training schedule; (3) post-training diagnostic test that will determine trainee level (compared to a pre-test baseline diagnostic test); (4) any combination of all the above.

Sessions become available to the users based on the definition of the guided exercise program (determined in stage 2). As soon as enough time has elapsed after the performance of the previous session performed on stage 1, or alternatively immediately if a specific schedule was not assigned, a guided session is unlocked and becomes available (stage 3).

In stage 4, the user performs this session once it is unlocked. The session is based on the above described methods of FIGS. 4 and/or 5.

Additional motivational elements may be introduced to incentivize participation and to encourage the desired game behaviors (considering the regular feedback delivery and reward system may not be sufficient in a lower frequency/ more standalone type of use), as shown in stage 5.

Optionally, after performing a session, an inter-session break is initiated (stage 6). The break ensures that the user is not ahead of the schedule defined in stage 2.

Optionally, stages 3-6 are performed more than once, as defined by the program assigned in stage 2. Moreover, stage 2 may also reoccur if needed, and adapt the program as needed.

Figure 7A:
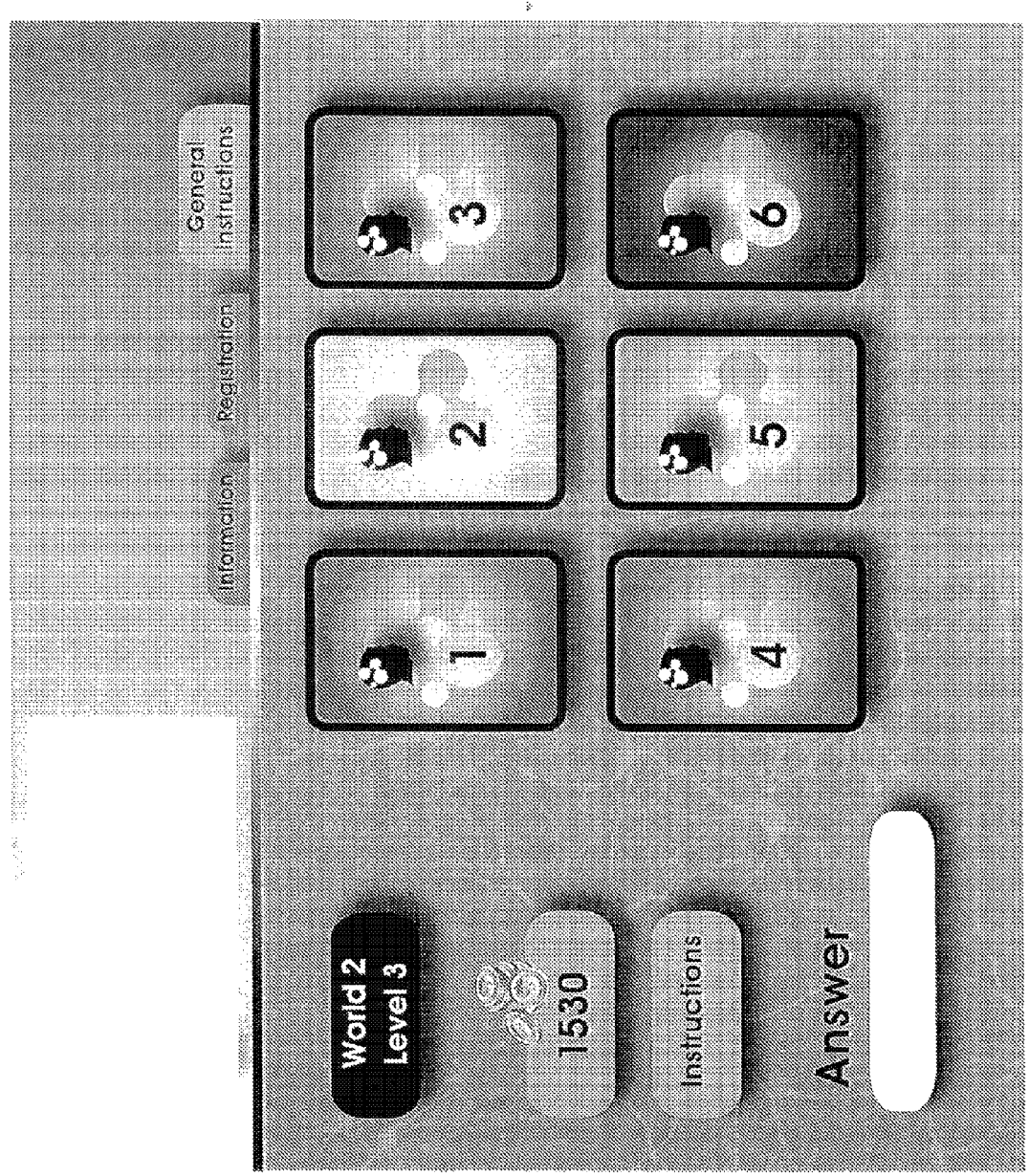
Figure 7C:
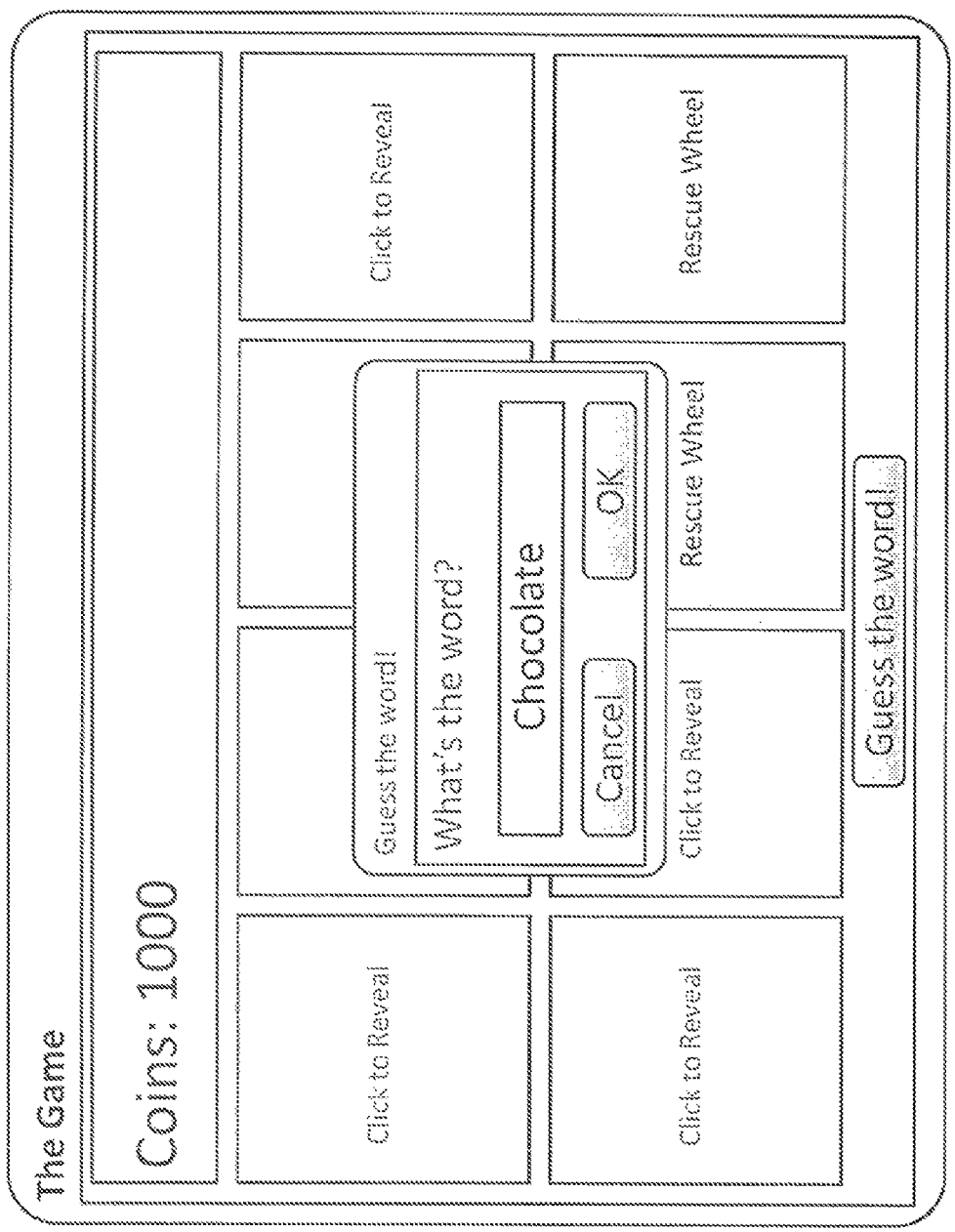

FIGS. 7A-C show exemplary non-limiting illustrative screenshots according to various embodiments of the present invention when implemented as a game, in which the user enters the word or words that are the solution to the linguistic task in the space provided.

Figure 8:
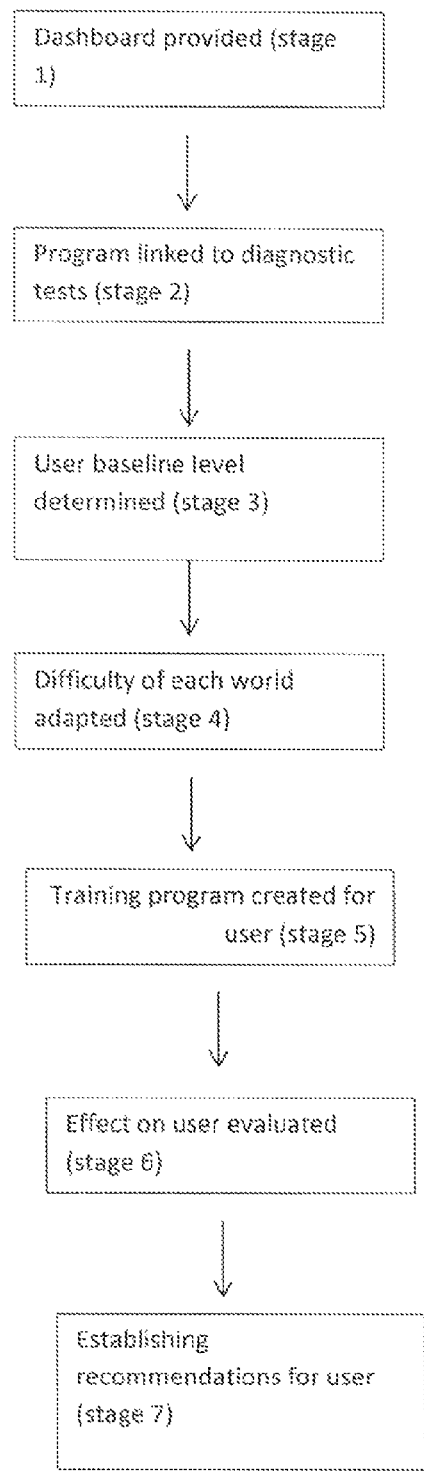
FIG. 8 relates to an exemplary method for improving a semantic ability of a subject with a semantic deficit according to at least some embodiments of the present invention.

FIG. 8 relates to an illustrative, exemplary, non-limiting method for handling abnormal semantic abilities according to at least some embodiments of the present invention, for example optionally with a speech therapist.

The method may optionally be very similar to that of FIGS. 4 and 5; however, optionally and preferably the below stages are interleaved with the methods of these figures.

The training program may be efficiently implemented in various clinical adult populations with either developmental or acquired language disabilities, such as language and learning disabilities or aphasia. It can be used as part of a clinical language therapy program to enhance multifarious language abilities, and can be easily adapted to meet the individual needs of each client. This can be achieved either during a therapy session or in between therapy sessions. In the first case, the language therapist will directly support the training process. In the latter, the speech therapy session will tap skills that the client will later practice in the comfort of his own home. In both cases, the software will enable the therapist to track the clients' achievements and difficulties thus allowing for refinement of the language treatment plan.

Optionally and preferably, in stage 1, the adaptation of the training program for therapeutic context includes provision of a dashboard for the therapist, which would allow him/her to monitor trainee's progress, and customize the training program to the unique needs of each client. The customization is based on system recommendations (based on data that will be entered on performance in external linguistic assessments, as well as data on training performance drawn from the training program itself). In addition, the therapist could set the number of sessions and each session length (based on preset ranges), place higher emphasis on training specific sub-skills, determine whether sessions will be performed alone or with a facilitator (the therapist or other care providers/peers), and the initial difficulty level of the program. The interface will enable customized alerts on client's performance and progress (e.g., 'client XX did not complete all sessions this week', 'client solved 20% of the stages—the program might be too hard!').

In addition, in stage 2, the program is linked to the state of the art diagnostic batteries assessing the relevant symptoms, in a way that permits the following stages to be performed: stage 3—determine the baseline level of each participant; stage 4—adapt the difficulty level for each type of world accordingly; stage 5—create a tailored training program that will include an optimized mix of worlds according to the baseline and treatment length; stage 6—evaluate the training-driven relief in the symptoms during and after the training; and stage 7—establish recommendations for follow up/maintenance sessions.

EXAMPLES

The below Examples relate to different experiments performed in the context of testing various embodiments of the present invention. This study explored the effect of a novel theory-based intervention intended to enhance semantic skills. A cognitive training program was developed based on theories and empirical findings which describe the role of the right hemisphere (RH) in semantic processing. The importance of RH linguistic processes to daily communication has been emphasized in recent neurolinguistic research, allowing to create a selective intervention to stimulate and enhance these processes in a way that will affect real life performance. In order to evaluate the effectiveness of the training and its selective effect on semantic performance (as opposed to general verbal and non-verbal skills), an experiment with an active control group was conducted. Fifteen participants used the computerized training program for five weeks and 15 participants trained on a non-semantic control program using the same game-like platform, stimuli and feedback.

In a semantic-relatedness judgment task, administrated before and after the training, significant post-training enhancement was observed among the training participants, compared to the control group. This enhancement was predicted by shifts in laterality indices along the training, so that participants with increasing RH (right hemisphere) bias showed more improvement on the semantic task. Moreover, the training group did not show any significant enhancement in any of the verbal and non-verbal control tasks—implying that the training effect was selective to semantic processing.

These findings provide preliminary evidence for transfer of the coarse semantic training. They are discussed from an applied perspective, with the conclusion that applying current knowledge on semantic processes successfully resulted in a non-invasive enhancement of semantic abilities, which may be used to affect semantic processing in daily life; and from a theoretical perspective, describing the contribution of this study to the body of knowledge on RH involvement in semantic processing.

1. Methods
1.1. Participants

Thirty volunteers participated in the study (14 males, ages: 20-29, mean age: 23.47). All participants were right handed, as assessed by the Edinburgh handedness inventory (Oldfield, 1971). All participants were monolingual, native Hebrew speakers, and were never diagnosed with learning disabilities or attention deficits. Participants were pseudo-randomly assigned to the training and control groups (15 participants in each group—seven males and eight females), and were blind to the experimental condition. Participants received 420 NIS (equivalent to 110$) for their participation.

1.2. Design

A pretest-posttest with active control group design was used (Campbell & Stanley, 1963). This design has numerous strengths in reducing internal validity threats, to which cognitive training studies are usually susceptible (Shipstead, Redick, & Engle, 2010).

1.3. Materials
1.3.1. Training Program

A computer assisted coarse semantic training program and an equivalent non-semantic control training program were developed. Following other successful training programs, the training program comprised 10 sessions (Gopher et al., 1994; Willis et al., 2006). On each level, participants had to find a single solution word, based on the 3-7 clues available on the screen, and level-specific instructions. Each program included 67 levels, composed from a pool of 396 clues. Training duration was not fixed, so that each training session included a pre-determined number of levels (intended to induce at least 30 minutes of training per session), and the session ended once the participant completed all levels.

1.3.1.1. The Basic Task

In the semantic training program, the basic task was designed following the three semantic processes that were described by the BAIS model (Jung-Beeman, 2005). On each level, participants were provided with different clues which were intended to activate different concepts in their minds. The participants had to open the clues one by one, in search of a single solution word that connects all the clues. To reach the solutions, participants had to integrate the activated concepts and select one outcome as the solution. For example, during a certain level, the participants can be presented with the four clues appearing in (shown in FIG. 9). The solution word for this level is "day", a single concept that all clues are remotely connected to (as detailed in Table 1). In the control program, the basic task did not involve any semantic activation, integration or selection. As in the training program, participants were instructed to use the clues on each level to find a single solution word. However, the integration of clues that was required in order to find the solution was based on non-semantic abilities, such as counting elements in the clues, scanning the clues for rhymes and categories (i.e., colors, numbers, action words, etc.) or for inflections of a specific word (i.e., smile, smiling), etc.

In the semantic training program, a tailored reward scheme was used in order to encourage participants to perform the basic training task thoroughly, i.e., activating and integrating distant meanings and selecting only the appropriate directions. The reward scheme was composed of three elements: (1) Level Scoring: the participants were most rewarded for using as few clues as possible, in order to challenge the integration of weakly related clues; for viewing each clue only once, in order to challenge meaning retention; and for reaching the solution on the first guess, in order to challenge selection. (2) Bonus Levels: At the end of each session, participants encountered a bonus level with six clues from previous levels, which served as recall cues. Participants received points for each solution they recalled in response to one of the clues. Vast literature on memory shows that performance in cued recall tasks is affected by the processing level of the target items—optimal performance in this task is achieved when deep semantic processing of the targets is performed (e.g., Craik & Lockhart, 1972; for review see Brown & Mitchell, 1994). This task served as an additional incentive for participants to deepen the processing of clues. (3) Extreme Levels: After concluding the post-training assessment, participants were presented with two difficult levels. The task and clues followed the usual training protocol; however the difficulty level was elevated by presenting elements from different game worlds, hence integrating different trained skills. Participants were informed at the beginning of the study that they will be rewarded up to 100 NIS (about 25$) for solving these levels, and were told that following the instructions and training protocol will increase their chances to complete the bonus levels.

In the control program, the rewarding scheme was altered, so that (1) level scoring encouraged participants to use all clues and emphasized the penalty on wrong solutions; (2) bonus levels at the end of the session included previously unseen trivia questions instead of clues (in order to avoid memorizing the relations between clues and solutions). Nevertheless, extreme levels were described and presented to both groups in a similar fashion, in order to encourage both groups to follow the protocols equally.

1.3.1.2. The Linguistic Stimuli

The pool of clues served as the linguistic stimuli, and it was used for both programs. In the semantic training program, the stimuli were manipulated so that they will trigger coarse coding by incorporating semantic tasks related to RH semantic processing. Most clues required the activation of distant related meanings (Jung-Beeman, 2005), or unusual interpretations (Abdullaev & Posner, 1997; Seger et al., 2000). With some clues, participants were requested to read passages with no titles—a task shown to elevate RH activity in an imaging study (St George et al., 1999). Other clues included tasks such as completing an endless sentence—based on increased involvement of the RH in finding optimal sentence endings (Kircher et al., 2001); selecting an appropriate ending for an endless joke (Coulson & Wu, 2005; Marinkovic et al., 2011); associating an idiom to an image related to its literal meaning (Mashal, Faust, Hendler, & Jung-Beeman, 2008); finding associations that connect two indirectly related words (Kiefer et al., 1998; Sass et al., 2009); or answering comprehension questions regarding excerpts that imply causal inferences (Virtue et al., 2008). In order to create a rich training environment (Gopher, 2007), the stimuli varied across different loads (from a single word to 2-3 paragraphs), modalities (written text, spoken text, songs, images and sounds) and task difficulty.

In addition to the clues, which were related to the solution word on each level, participants were also presented with 1-4 surprises on each level. About 40% of the surprises were linguistic stimuli which were manipulated just like the clues, and 60% simply awarded the participant with bonus points. The surprises were incorporated in the training program in order to increase the exposure to the linguistic stimuli and to the integrated coarse semantic tasks without loading the game levels with additional clues. Opening surprises was always rewarded with points, which served as an incentive to approach them.

The linguistic stimuli used in the non-semantic control program were slightly adjusted in order to avoid the triggering of coarse semantic processing. For instance, no words were missing in the sentences, texts were provided with titles, and no instruction prompted activation of related meanings. The surprises were replaced with multiple choice trivia questions (while maintaining the 40:60 proportions of the linguistic stimuli and bonuses).

1.3.1.3. The Training Program

For the coarse semantic training program, 10 types of game worlds were used, each placing an emphasis on a certain subcomponent or a specific set of demands that were identified in the neuro-cognitive literature as integral to coarse semantic processing. Examples include distant meaning retention (e.g., Burgess & Simpson, 1988), suppression of distracting meanings (e.g., Tompkins, Baumgaertner, Blake, & Fassbinder, 2000), activating literal and figurative non-salient meanings (e.g., Giora & Stringaris, 2009), and the integration of previous context in order to elicit more meanings (Federmeier, 2007). Moreover, in order to induce variability and allow trainees to explore the trained skill under different demands (Gopher, 2007), additional variables were manipulated between game worlds: time for processing a clue, mental load (clue complexity and length) and the number of clues available.

The different subcomponents were emphasized in each game-world by introducing different instructions, exposing participants to different sets of stimuli and modifying the reward scheme. For instance, in worlds which emphasized different meaning types, some clues were related to the solution through their figurative meaning and some through their literal meaning, and the surprises included tasks such as associating an idiom with an image that was related to its literal meaning. In worlds which manipulated mental load, the number of clues and surprises was higher, and many clues included long excerpts. In worlds which emphasized meaning retention, the cost of re-opening a clue was higher, and so was the penalty for wrong guesses.

Each world included up to four levels. Easier levels were placed in the beginning of each session or following a sequence of more difficult levels. The worlds were introduced gradually by their difficulty level, with repetition between the sessions. The first seven sessions included two worlds, typically—one reoccurring type and a new one. The last three sessions contained 3-5 worlds each with fewer levels on each world, so that more world types reoccurred on each session and the emphasis on change was more frequent. All in all, the training program became more difficult as it progressed due to the integration of more difficult worlds, more difficult levels, and more frequent changes between worlds towards the end of the program. Game-level difficulty was manipulated by a combination of factors, including the number of clues (assuming that more clues induce a higher load), the salience of the embedded element in the clue which related it to the solution (assuming that addressing the non-salient elements in the clues is more demanding), and the remoteness of the association between the clue and the solution.

The control program did not employ the emphasis change protocol. Thus, the game worlds did not differ by an emphasized subcomponent. Nonetheless, the program's superficial structure was identical to that of the training group—including the number of levels in each world and number of worlds per session. As in the training program, easier levels were incorporated at the beginning of each session or following a sequence of more difficult levels, and task difficulty rose as the program progressed.

1.3.1.4. Feedback Content and Schedule

Given that previous research has shown that in the context of cognitive training, intermittent feedback enhances transfer (Gopher, 2007; Schmidt & Bjork, 1992), and formative feedback is superior to basic Knowledge of Results (KR) feedback (Shute, 2008), intermittent formative feedback was integrated at the end of each world and session. The feedback provided participants with elaborate Knowledge of Results (KR) which related their performance to the high-level training objectives of the specific world and their expression in real-life language processing and suggested tips for improvement. Additional simplified KR feedback was provided immediately following any input from the participant. The feedback schedule was identical in both programs, and the performance in both programs was related to the same high-level training goals. Minimal adjustments were made in the control program feedback content in order to maintain coherence with the content of the specific levels. As a result, the feedback which was provided to the control group was less specific.

1.3.1.5. Pretests

During the development of the training and control programs, formative evaluations were performed by observing individuals from the target population performing early versions of the program in lab settings. Based on these observations, the instructions, reward schemes, level difficulty, program structure and content on specific clues and levels were adjusted. These observations assured that trainees who used the training version utilized the expected thinking processes in general and as a response to the different emphases in particular, and that trainees in the control version did not use similar semantic operations to solve the different levels.

1.3.2. Pretest-posttest Battery 1.3.2.1. Semantic Task: Relatedness Judgments Following Ambiguous Prime Words Reason for inclusion in the battery. In order to evaluate the effectiveness of the semantic training and its selectivity in RH semantic processes, the first task in the battery was a semantic task that probes RH and LH semantic processing. Previous studies which utilized judgments on ambiguous words have demonstrated that the semantic activation of meanings related to ambiguous words is lateralized according to meaning saliency (Burgess & Simpson, 1988; Peleg & Eviatar, 2008, 2009, 2012). In line with the prediction of the BAIS model (Jung-Beeman, 2005), these studies show that responses to words that are related to the subordinate meaning of an ambiguous word ('BANK'—riverside), presented at least 250-750 ms after the ambiguous word, are considered to reflect coarse semantic processing in the RH, while responses to the dominant or salient meaning ('BANK'—financial institution) reflect LH semantic processing. Most importantly, this task was also used before in Hebrew in order to examine changes in RH and LH related semantic performance separately, following brain stimulation (Harpaz, Levkovitz, & Lavidor, 2009; Peretz & Lavidor, in press).

Stimuli. The stimulus pool consisted of 160 Hebrew ambiguous words which served as primes (i.e. LEVANA, in Hebrew: white/moon). The target words, ranging between 2-7 letters, were either related to the prime word's dominant meaning (i.e., "red", related to the dominant meaning "white"), to its subordinate meaning (i.e., "night", related to the subordinate meaning "moon"), or completely non-related (i.e., "shower"). The semantic relations have been validated in previous studies (Faust & Kahana, 2002; Harpaz, Levkovitz, & Lavidor, 2009; Peleg & Eviatar, 2008). Two equivalent stimuli lists were created, each including 80 ambiguous words. No words were repeated as prime/target words on the same list.

Design. The semantic task comprised three conditions which was characterized by the type of relation between the prime and target words (dominant/subordinate/unrelated). The subordinate relation type condition was therefore used as the critical condition for the evaluation of the semantic processing that is related to the right hemisphere.

The stimuli were pre-allocated randomly to the different conditions, so that in each list 20 words were allocated to the dominant condition, 20 to the subordinate condition, and 40 to unrelated condition. Length and frequency of each type of word (prime and target) were matched between conditions.

Following previous studies which employed the same stimuli (Harpaz et al., 2009), a block design was used based on relation type. One block contained all the dominant-related trails and one block contained all the subordinate-related trials. Each block included an equal number of related and unrelated trials.

Procedure. The participants were comfortably seated in a quiet room, with a chin rest fixating their gaze at a distance of 57 cm from the screen. The screen sampling rate was 60 Hz. The stimulus display was controlled by an E-prime 1.1 software (Psychology Software Tools, Inc., PA, US).

The participants were presented with short instructions on the screen, followed by eight practice trials in which they received feedback for their responses. In the first four practice trials, participants were required to perform a relatedness judgment for unambiguous words. Following an additional explanation of the concept of ambiguous words, four more practice trials were performed—this time with ambiguous words as primes. Following a short debriefing, the experiment began.

The experiment included two blocks which presented in random order, with a 30 second intermission between blocks. Each block contained 20 related and 20 unrelated trials, presented in random order.

Each trial began with a central fixation cross, which was presented for 500 ms, followed by the prime word, which was presented in the center of the screen for 180 ms. A fixation cross re-appeared for an additional 500 ms, followed by the presentation of the target word in the center of the screen for 180 ms. Then, participants were instructed to indicate whether the target word was related to the prime word or not. The participants responded by pressing one of two keys with the right index or middle fingers.

Measurement. Performance in each condition was measured by response time (RT) for correct answers, as well as accuracy rate (ACC). An integrated performance measurement was created by dividing the RT by ACC, so that lower scores reflected better performance.

1.3.2.2. Verbal Memory Test: A Subset of the Rey Auditory Verbal Learning Test (AVLT)

Reason for inclusion in the battery. We suspected that the requirement to integrate verbal information from different clues, which is presented in both training programs, would elicit some memory enhancement. Hence, we aimed to include a verbal memory test in the test-retest battery, in order to examine whether memory was enhanced following the training, and whether that enhancement mediates semantic training-induced effects.

We selected the Rey Auditory Verbal Learning Test (AVLT, Rey, 1941, 1964) in order to measure different aspects of verbal learning and memory (Vakil & Blachstein, 1993). A Hebrew version of this test is widely used for academic and clinical purposes, and detailed norms are available (Vakil & Blachstein, 1997). The structure analysis performed using the Hebrew version indicates that the test scores reflect more than one verbal memory domain and provide valid measurement for processes that are related to acquisition, retention and retrieval (Vakil & Blachstein, 1993). Notably, the English version of this test was reliably used before in a test-retest design and showed good reliability when using equivalent versions (Geffen, 1994).

Stimuli. Stimuli were taken from the Hebrew version of the Rey AVLT (Vakil & Blachstein, 1993). The test includes two lists of 15 common nouns. These lists were used as two equivalent versions of the verbal memory task.

Procedure. The procedure followed the standardized administration of the 1-5 Rey AVLT trials, as described by Lezak (1983). The participant was sitting in front of the experimenter, and the test was administered orally. The list of words was read to the participants at a rate of one word per second, five consecutive times. Each reading was followed by a free recall task, in which participants were requested to repeat all the words they could remember, regardless of the order in which they were read.

Measurement. Following Vakil & Blachstein (1993), four measurements were derived from the test. They reflect different factors which are associated with memory processes: immediate memory (trial 1 score), reflecting the initial recall and related to acquisition processes; best learning (trial 5 score), reflecting the recall on the final trial and related to the retention and retrieval processes; learning rate (trial 5 score minus trial 1 score), reflecting the learning ability of the participant while placing less emphasis on the initial recall, with relation to the acquisition processes; and total learning (sum of scores on all 5 trials), reflecting the capacity to recall and accumulate words across learning trials, with relation to the retention process.

1.3.2.3. Lexical Task: Lexical Decision

Reason for inclusion in the battery. The aim of the training program is to improve coarse semantic processing. However, it is possible that due to the engagement with verbal stimuli, the enhancement induced by training will not be limited to semantic processes—it may enhance verbal abilities in general, or at least, RH verbal abilities that are not semantic per se. Moreover, it could be argued that the effects which are observed following the training in the semantic task are merely an artifact of enhancement in low-level linguistic abilities. Therefore, we intended to test the selectivity of the training by probing non-semantic low-level linguistic processing in general, and in the RH in particular. It has been established that lexical access to familiar written words occurs before the semantic system is activated, as agreed by numerous well-accepted models of word reading (for review, see Coltheart, 2006). Thus, it was decided to probe the lexical aspects of word recognition by using a lexical decision task, a common task used to investigate visual word recognition and to probe lexical access (e.g., Balota & Chumbley, 1984; Hudson & Bergman, 1985).

Stimuli. The stimulus pool consisted of 120 five-letter Hebrew words, and 120 five-letter non-word strings. Two equivalent stimuli lists were created, each including 60 words and 60 non-words. Analysis of Variance (ANOVA) revealed no difference between lists in word frequency ($F<1$).

Design. The lexical task comprised six conditions (2×3): word type (word/non-word)×presentation (central visual field (CVF)/right visual field (RVF)/left visual field (LVF)). Brief lateralized presentation of words to the left or right visual fields allows us to probe the processing of these stimuli in the contra-lateral hemisphere, a common technique often referred to as the divided visual field (DVF) paradigm (Bourne, 2006). Thus, a presentation of words to the LVF was used as the critical condition for non-semantic verbal processing in the RH, while the presentation of words across all three presentation conditions was used as a general test for non-semantic verbal processing. For each participant, the stimuli were randomized across the presentation conditions.

Procedure. As in the semantic task, participants were seated at a fixed distance of 57 cm from the screen. The stimulus display was controlled by an E-prime 1.1 software (Psychology Software Tools, Inc., PA, US). The participants were presented with short instructions on screen, followed by six practice trials—one of each condition, presented in random order. Following each practice trial, accuracy feedback was provided. Following a short debriefing, the experiment began.

The experiment included 120 trials which were presented in random order, with a 30 second intermission after the first 60 trials. On each trial, one of three presentation conditions was assigned randomly. In the CVF condition, words were presented in the center of the screen; in the lateralized conditions words were presented 2.57° from the center of the screen (so that the near edge of the word was 2.55 cm from the center).

Each trial began with a central fixation cross, presented for 1000 ms, followed by the stimuli, presented in the RVF/CVF/LVF for 180 ms. Then, participants were instructed to indicate whether the string presented was a Hebrew word or not. The response was made by pressing one of two keys with the right index or middle fingers. Response time limit was 1700 ms.

Measurement. As in the semantic task, an integrated performance measurement was calculated for each condition by dividing RT (for correct answers only) by ACC. Lower scores reflected better performance.

1.3.2.4. Non-verbal Task: Lateralized Coherent Motion Detection (CMD)

Reason for inclusion in the battery. The final task on the test-retest battery was dedicated to evaluating change in non-verbal processing in the right and left hemispheres. This was done in order to assure that enhancement in RH processes that were induced by the training is not general, but rather selective to semantic processing. Therefore, we utilized a lateralized version of Coherent Motion Detection (CMD), a well-established task that is used for the probing of the visual system, and the magnocellular system in particular. In this task, participants are exposed to arrays of moving dots, where some of the dots are moving coherently to the same direction, and other dots move at random. The participant's ability to recognize the coherent motion when only small portions of the dots are moving coherently reflects the proficiency of the magnocellular visual system.

Stimuli. Stimuli, design and procedure followed Levi, Walsh & Lavidor (2010). The stimulus consisted of two random-dot-kinematograms which contain 300 dots each. The grey dots appeared over a brighter grey background (brightness ratio dots/background=0.57) and were 0.14 cm in size. The two arrays were presented simultaneously one beside the other, so that each array was perceived by one visual field. Coherent motion was created as the movement of a certain percentage of dots in a single, randomly chosen direction. The rest of the dots, as well as the dots in the other array, moved in random directions. Apparent velocity was approximately 1 degree per second.

Design. The non-verbal task comprised three conditions that were characterized by the appearance of coherent motion in either of the arrays (right (RVF)/left (LVF)/none (No-coherence)). The RVF and LVF presentation conditions were used to probe non-verbal processing, whereas the LVF condition probed for non-verbal processes in the RH in particular. The no-coherence condition was introduced in order to prevent a possible strategy of looking constantly at one of the arrays. RVF and LVF conditions appeared in equal proportion of the trials (40% each), while the no-coherence condition appeared on only 20% of the trials.

Procedure. As in the semantic and lexical tasks, participants were seated at a fixed distance of 57 cm from the screen. Thus, each array of dots occupied 9.2°×13.5° of a visual angle, and dot size was about 1.5°. The arrays were presented at a distance of 4.9 cm, with a fixation cross between them in the center of the screen, so that each array appeared 2.5° to the right or the left of fixation. The stimulus display was controlled by MATLAB 7.0 software.

The participants were presented with short instructions on screen, followed by 20 practice trials that were identical to the experimental trials and did not include any feedback. Each trial began with a central fixation cross, which was presented for 500 ms, and followed by a 500 ms motion period. On each trial, coherent motion could appear in one of the arrays, while random motion appeared in the other one (in the no-coherence condition, random motion appeared in both arrays). Participants were instructed to indicate whether coherent motion appeared in the right array, the left array, or in none of the arrays. They responded by pressing one of three keys with the right index finger, with no time limit.

The degree of motion coherence was manipulated by changing the percentage of the dots that move in the same direction. The manipulation was done for each condition separately, based on each participant's individual performance in the previous trials in that condition. In the first trial of the practice and the experiment, the degree was 63%. A 3-down 1-up staircase procedure was used, so that the percentage decreased by 3% after three consecutive correct responses, and increased by 3% after an incorrect one.

To gather the minimal amount of data that is required for the calculation of a reliable performance measure, the experiment length was also determined by performance. Unless a maximal limit of 400 trials was exceeded, the experiment ended after at least 15 reversals in each condition. Reversals were defined as a change in the coherence trend, i.e. a decrease in the degree of coherence after a period of increases or vice versa.

Measurement. The performance measure was the coherency threshold which was calculated separately for each condition as the average of coherence values over 12 reversals. As the number of reversals varied between conditions and participants, only the values of coherency at the last 12 reversals in each visual field were included in the threshold calculation. Lower coherency thresholds indicate better performance.

1.3.3. Additional Measurements

In order to characterize the training effects, prior motivational, scholastic and verbal abilities were evaluated. Additionally, in order to gain an additional perspective on training induced plasticity, behavioral laterality indices were measured throughout the training 1.3.3.1. Trait Motivation: BIS/BAS Scales Trait motivation was assessed by using a Hebrew online version of the BIS/BAS scales (Carver & White, 1994). The questionnaire comprises 24 items (four fillers). All items were judged on a four-point scale, ranging from 1 ('I strongly agree') to 4 ('I strongly disagree'). The BIS/BAS scales assess a behavioral inhibition measure (BIS; calculated as the sum of the scores of seven items, i.e., "I worry about making mistakes") and three behavioral approach measure (BAS) subscales: BAS Reward Responsiveness (BAS-RR, which measures positive anticipation of rewarding events, i.e., "When I see an opportunity for something I like I get excited right away"), BAS Drive (BAS-D, which measures rewards pursuit, i.e., "I go out of my way to get the things I want") and BAS Fun Seeking (BAS-F, which measures the search for new rewarding situations, i.e., "I'm always willing to try something new if I think it will be fun"). The BAS scale is calculated as the sum of scores in the 13 items which compose these subscales.

1.3.3.2. Prior Verbal and Scholastic Abilities: Psychometric Entrance Test (PET) Total and Verbal Scores The PET is a scholastic aptitude test which is constructed and administrated by the Israeli National Institute for Testing and Evaluation (Beller, 1995). The test is intended to estimate future success in academic studies, and is considered highly reliable. For many years, it has been a mandatory part of the university admission process in Israel (Beller, 1994). The total score is a normalized weighted average of three multiple choice subtests: verbal reasoning (40%), quantitative reasoning (40%) and English as a foreign language (20%). In particular, the verbal reasoning subset comprises 60 items of different types and is focused on the ability to analyze and understand complex written material, the ability to think systematically and logically, and the ability to perceive fine distinctions in meaning among words and concepts (Beller, 1994, p. 13).

Participants were requested to share their total and verbal scores. Sharing these scores was not communicated as a prerequisite for participation.

1.3.3.3. Laterality Index: Line Bisection

Line bisection is a behavioral assessment method for laterality which was initially designed to identify unilateral neglect (for review, see Jewell & McCourt, 2000). Recently, it has been confirmed as a valid measure for prefrontal asymmetry (Nash et al., 2010).

On each trial, participants were instructed to mark the exact center of a 170 mm horizontal black line, using a fine-point pen. Each line was printed in the center of a blank A5 landscape paper. The papers were bound in 80 pages booklets. On each measurement, participants performed three trials of this task. Participants were instructed to perform a 3 trial measurement before and after each training session. At those times, the training program prompted a reminder for the line bisection task, referred the participant to a specific page in the booklet, and indicated a unique eight character code the participant had to write on that page, for retrospective verification purposes.

Scores reflected the average percent of deviation from the midpoint of the line, so that positive scores reflected a bias to the right side and to the contra-lateral left hemisphere (LH bias) and negative scores reflected a bias to the left side (RH bias).

1.4. General Procedure

Volunteers filled in online demographic and personal information questionnaires, as well as the Edinburgh handedness inventory (Oldfield, 1971). Participants who matched the participation criteria additionally completed the BIS/BAS scale (Carver & White, 1994) and reported their PET total and verbal scores (Beller, 1994, 1995). Then, the participants were pseudo-randomly assigned to the training and control groups.

Subsequently, each participant arrived at the lab for the pre-training assessment session. After signing the consent form, participants completed the four tasks that were included in the test-retest battery (semantic task, memory test, lexical task and CMD task). The order of the non-semantic tasks was counterbalanced across participants. The order of the test versions was also counterbalanced. The evaluation lasted for 40-60 minutes, and was followed by an introduction to the training program.

During the training introduction, the participants launched the training program, followed the instructions and completed three levels. In the beginning, they were prompted to perform the line bisection task. The experimenter facilitated the session and emphasized the guidelines that are related to the game rules, the training protocol and schedule, the reward scheme and the line bisection task. Participants received a game CD and installation instructions, and were instructed to install the program and begin the training at home 2-5 days following the lab session.

Participants performed 10 training sessions at home, and were instructed to perform the training in a quiet room with no observers. The participants completed two sessions per week, and had a weekly conversation with the experimenter for questions and feedbacks. 2-5 days after the last training session, each participant arrived at the lab to complete the post-training assessment session. The session procedure was identical to that of the first session. Following the evaluation, the participants completed two 'extreme levels', and were rewarded with an extra 50 NIS for each level they solved. It is important to note that throughout the study, the procedure was identical for participants in both groups.

2. Results

All 30 participants completed the intervention and assessments according to schedule, without any compliance issues or dropouts. Analyzing performance logs during the experiment, the experimenters noticed no transgressions in the performance, and made sure that all participants progressed as expected in the program. Thus, data from all 30 participants was included in the analyses.

To ensure that the groups did not differ in relevant a-priori characteristics, a series of t-tests for independent samples was conducted. As detailed in Table 2 (FIG. 10), the analyses did not reveal any significant differences between the groups in the various demographic, motivational and cognitive measures that were assessed prior to their participation.

To make sure that the groups' performance before training did not differ, another series of t-tests for independent samples was conducted. As detailed in Table 3 (FIG. 11), prior to the training, no significant differences were found between groups in any of the tests.

As no significant differences were found on the pre-training assessment, we used a unified measure for all tests. This measure represents the change between pre and post-training assessments. To account for prior individual differences among the participants, the change measures were weighted against each participant's baseline performance. The individual performance change measures were calculated by subtracting the pre-training performance from the post-training performance, and dividing that by the pre-training performance (multiplied by 100, to create a percentage). For the semantic, lexical and non-verbal tests, where improvement reflected as lower scores post-training, change was calculated by subtracting the post-training from the pre-training threshold, and dividing that by the pre-training threshold (multiplied by 100). Thus, for all tests, higher scores reflected a larger individual training gain.

Figure 12:
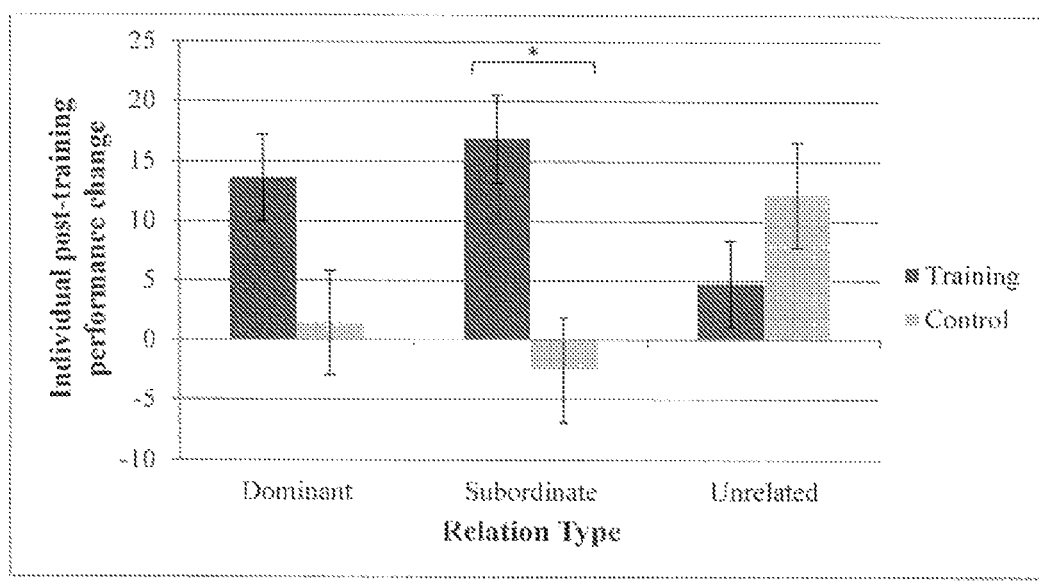

To test the effectiveness of the semantic training, performance change in the semantic task was analyzed by a mixed-design ANOVA with the group as the subject factor, relation type (dominant/subordinate/unrelated) as the within-subject factor, and individual change in integrated performance (RT/ACC) as the dependent measure. As illustrated in FIG. 12, while no main effects for the group or relation type were found, the analysis did reveal a significant interaction between group and type, $F(2, 56)=4.13$, $p=0.021$, $\eta^2=0.13$. In accordance with our hypothesis, a series of independent sample t-tests using Bonferroni correction for multiple comparisons showed that the interaction source was a difference between groups in the subordinate relation type condition, $t(28)=2.47$, $p=0.020$, so the training group showed training gain (M=16.88, SD=20.88) while the control group did not (M=−2.53, SD=22.22). No significant differences between the groups were found for the other relation types (dominant: $t(28)=1.91$, $p=0.066$; unrelated: $t(28)=-0.87$, $p=0.390$). This trend is also reflected by examining the raw pre and post-training scores by group (Table 4—see FIG. 13). Hence, training induced improvement in judging semantic relatedness of distantly related meanings for ambiguous words, but not for unrelated meanings.

Interestingly, in the control group, the insignificant individual change in the dominant relation condition (M=1.43, SD=16.80) highly correlated with the insignificant individual change in the subordinate relation type condition ($r=0.76$, $p=0.001$), which indicates that both related conditions were equally unaffected by training; while no such correlation was evident for the training group ($r=0.00$, $p=0.998$), where the change in subordinate condition was significant,—which indicates a different pattern of change in the RH and LH related processes in this task following the training.

FIG. 12 shows means and standard errors (SE) for individual post-training performance change in the semantic task, by group and relation type. Pre and Post-training performance was calculated as RT for correct answers divided by accuracy; change was calculated as [(pre-training−post-training)/(pre-training)]*100. Error bars represent standard error of the mean, corrected for individual subject means (Cousineau, 2005). *p<0.05

To evaluate the possible positive side-effect of both programs on memory skills, four mixed-design ANOVA were conducted, with the group being between subject factor and the time of measurement (pre/post-training) being within subject measurement. As detailed in Table 5 (FIG. 14), the analyses revealed significant improvement over time in three of the scores (immediate memory, best memory and total memory), while no differences were observed between the groups in any of the scores (nor were there any significant group X time interactions). Hence, enhanced performance in three of the four scores was observed following the training in both programs, however, no additional enhancement was observed following the semantic training.

Figure 15:
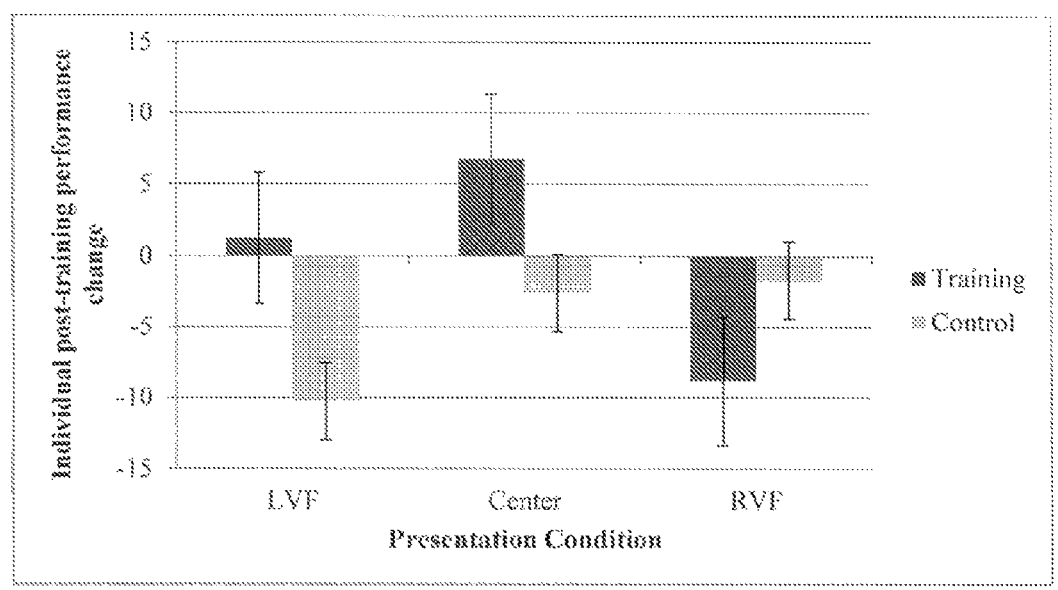

In order to test the selectiveness of the semantic training, two more mixed-design ANOVA were conducted on the additional non-semantic control tasks, much like the semantic task analysis. Performance change in the lexical task was analyzed by a mixed-design ANOVA with the group as the between subject factor, presentation condition (RVF/CVF/LVF) as the within-subject factor, and individual change in integrated performance (RT/ACC) in response to words as the dependent measure. As illustrated in FIG. 15, the mixed-design ANOVA revealed no effects for group or presentation condition (F<1), nor a significant interaction, $F(2, 56)=1.40$, $p=0.256$. The raw pre and post-training scores (detailed in Table 6, shown in FIG. 16) also do not indicate any post-training enhancement or group differences. Hence, in accordance with our hypothesis, the training did not induce improvement in recognizing words in a non-semantic verbal task, not even in the LVF condition that targeted the right hemisphere.

FIG. 15 shows means and SE for individual post-training performance change on the lexical decision task, by group and presentation condition. Pre and post-training performance was calculated as RT for correct answers divided by accuracy; change was calculated as [(pre-training−post-training)/(pre-training)]*100. Error bars represent standard error of the mean, corrected for individual subject means (Cousineau, 2005).

Finally, in order to evaluate changes in the non-verbal task, an additional mixed-design ANOVA was performed, with the group as the between-subject factor, the visual field (VF: RVF/LVF) as the within-subject factor, and individual change in coherent motion detection thresholds as the dependent measure. As illustrated in FIG. 3, the analysis revealed no group or VF effects (F<1), and no interaction between the group and VF, $F(1, 28)=1.16$, $p=0.291$. The raw pre and post-training scores which are detailed in Table 7 (FIG. 18) further show that both groups had similar performance before and after the training, which supports our conclusion that training did not induce improvement in the non-verbal task of detecting coherent motion, not even in the LVF condition that targeted the right hemisphere.

Figure 17:
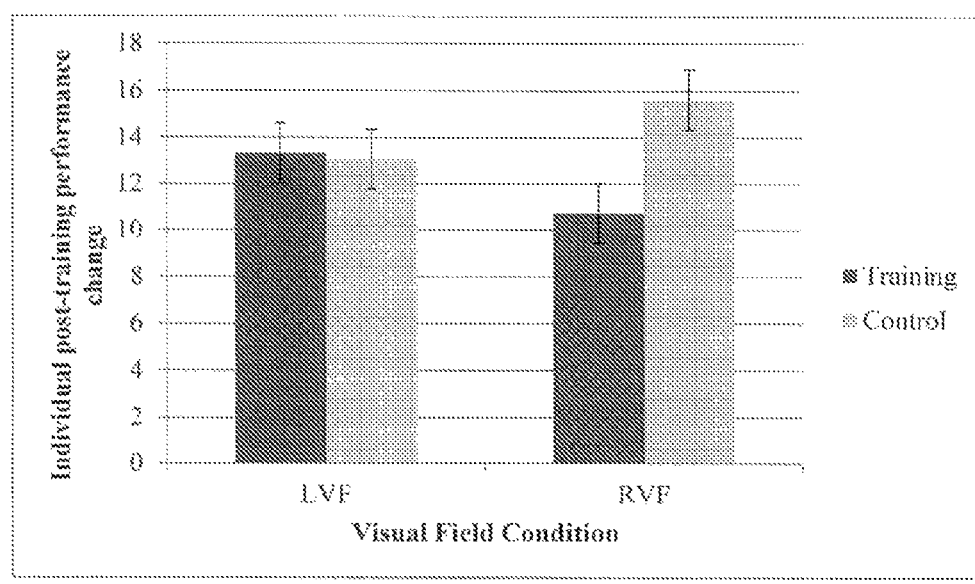

FIG. 17 shows means and SE for individual post training change in coherency thresholds on the coherent motion detection task, by group and visual field condition. Performance change was calculated as [(pre-training−post-training)/(pre-training)]*100. Error bars represent standard error of the mean, corrected for individual subject means (Cousineau, 2005).

As evident from Table 19, which presents a summary of the post-training effects in each of the four tests that are included in the pretest-posttest battery, in line with our predictions, the only significant difference between the groups was detected in the semantic task—where post-training enhancement was evident in the training group only, reaching a significant effect in the subordinate relation type condition; a marginally significant effect in the dominant relation type condition; and no effect in the unrelated condition. In order to characterize this effect and investigate possible factors which are specifically related to the training-induced semantic improvement, we performed three series of regression analyses.

The first set of analyses was aimed at testing the hypothesis that the cognitive changes that are evident in the semantic task were related to brain plasticity as reflected by individual laterality shifts that were measured along the training using the line bisection tasks. Individual laterality shifts were calculated for each participant by subtracting the arcs in the transformation of his/her average percentage deviation at the end of the last training session, from his/her arcs in the transformation of the average percentage deviation at the first training session. A higher positive laterality shift indicated a stronger RH bias that was developed along the training, while a lower negative shift indicated a stronger LH bias. Table 9 (FIG. 20) details the average individual change per group, as well as the raw deviations before and after the training. While participants in the control group exhibited a marginally significant LH bias ($t(13)=-2.08$, $p=0.057$), participants in the training group did not show any significant bias ($t(13)=-0.60$, $p=0.560$). However, the high variation between participants, especially in the training group, indicates that some individuals may have had a stronger shift than others.

Mean individual shifts are calculated by subtracting the arcsin transformation of each participant's average percentage deviation at the end of the last training session, from the arcsin transformation of the average percentage deviation at the first training session, averaged across participants; Positive shifts indicate RH bias.

Figure 24A:
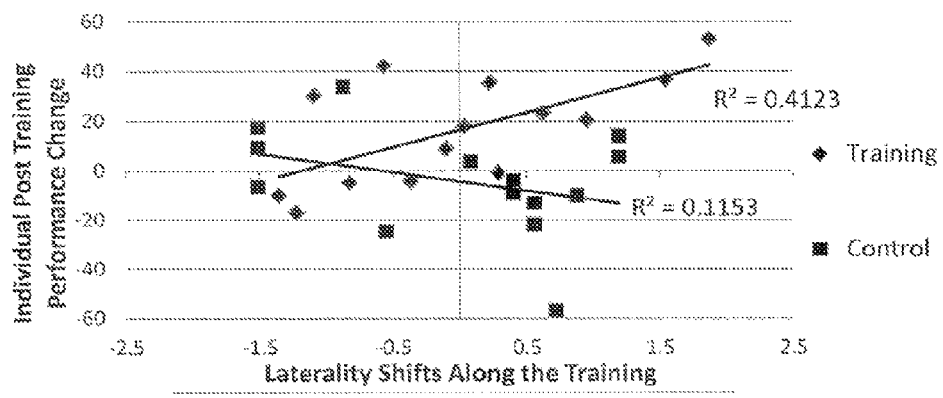

Therefore, a series of linear regression analyses were performed in order to predict the individual performance change in the different conditions of the semantic task by using the laterality shift as predictor. The analyses were done separately for the training and control groups. In the training group, training gain in the subordinate relation type condition was significantly predicted by the laterality shift, $F(1, 12)=8.42$, $p=0.013$, so that participants who developed stronger RH bias along the training exhibited greater improvement in identifying words that were related to the subordinate meanings of the ambiguous prime word (see FIG. 24a). The laterality shift accounted for 41.2% of the variability in performance change. As detailed in Table 10 (FIG. 21), no other regression equations were significant, therefore the laterality shift did not predict a performance change in either of the conditions in the control group, nor in the other two relation type conditions in the training group. Hence, the laterality shift selectively predicted the magnitude of the training-induced semantic effect.

Figure 24B:
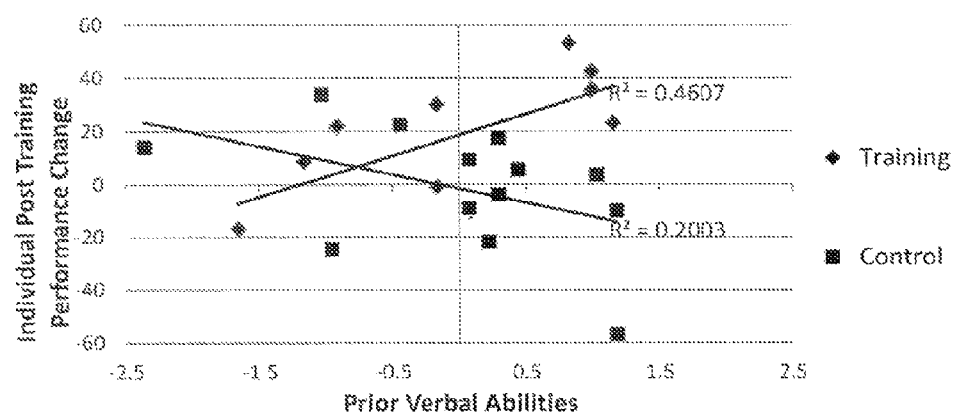

A second series of analyses examined whether prior linguistic abilities predicted the magnitude of the training induced effect. PET Verbal reasoning score, reflecting prior Hebrew vocabulary and reasoning abilities, was entered in a linear regression analysis in order to predict an individual performance change in the different conditions of the semantic task, for each group separately. As detailed in Table 11 (FIG. 22), prior linguistic abilities predicted the training-induced effect only, that is to say that the only significant regression equation was found when predicting the individual training gain in the subordinate relation type in the training group, $F(1, 8)=6.84$, $p=0.031$. Verbal abilities accounted for 46.1% of the variability in the training induced improvement, so that participants with higher prior abilities benefited more from the training (see FIG. 24b). Hence, prior verbal abilities selectively predicted the magnitude of the training-induced semantic effect.

Figure 24C:
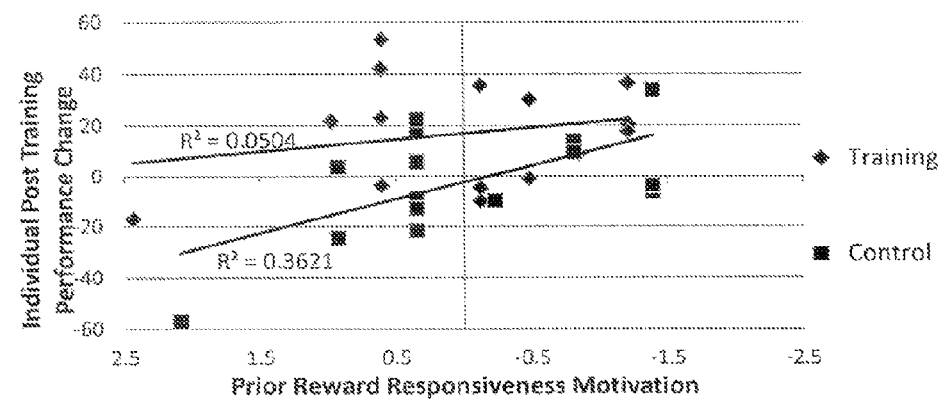

The final set of analyses was aimed at testing the effect of motivational factors on the participants' post-training improvement, in order to assure that the effect was not due only to the participants' sensitivity to rewards. To that end, two regression analyses were performed using the reward sensitivity score (BAS-RR) of the BIS/BAS scale as a predictor, in order to predict individual change in identifying words related to the subordinate meanings of the ambiguous prime word in the semantic task. As detailed in Table 12 (FIG. 23), while the training group reward sensitivity did not predict the performance change (F<1), in the control group reward sensitivity accounted for 36.2% of the variability in the performance change, $F(1, 13)=7.38$, $p=0.018$. Hence, the reward sensitivity motivational trait predicted the pretest-posttest improvement only in the control group, but not in the training group (see FIG. 24c).

FIG. 24. Individual pretest-posttest changes as predicted by (a) laterality shifts, (b) existing verbal abilities, or (c) reward responsiveness motivation, in each group. Individual changes were measured as post training performance change in the subordinate relation condition of the semantic task, and calculated as [(pre-training−post-training)/(pre-training)]*100. Laterality shifts were measured as post training change in the line bisection task, calculated using arcsin transformation of average percentage deviation as (end of the last training session−first training session), and standardized per group. Existing verbal abilities were measured as verbal PET score, reported by participants prior to the training, standardized per group. Reward responsiveness motivation was measured prior to the training as the BAS-RR subscale of the BIS/BAS scale, and standardized per group (note that lower scores indicate higher reward sensitivity).

3. Discussion

The main finding in our study was that the cognitive training developed, based on state-of-the-art literature on semantic processing in the right hemisphere, was effective. The training program resulted in significantly enhanced performance in an untrained semantic task. The improvement was evident in the training group only, although no differences between the groups were detected prior to the training. Since semantic relatedness judgments were not directly trained by the program, we conclude that we did not simply train the specific training task, but rather that we trained the underlying semantic processing mechanisms, which consequently improved and affected performance under different circumstances and context. These results serve as preliminary evidence for far-transfer of the training within the realm of semantic processing, i.e., post training performance improvements in a task that was different in nature from the trained task, tested in different physical, temporal and functional contexts compared to the training (Barnett & Ceci, 2002).

Specifically, the training of coarse semantic skills led to improvement in a condition probing for coarse semantic processing, namely—the activation of less salient meanings, that are distantly related to ambiguous prime words. The ability to activate and retain multiple salient and less salient interpretations for a given ambiguous stimuli or situation, also termed ambiguity tolerance, is considered key to creativity (e.g., Tegano, 1990; Zenasni, Besançon, & Lubart, 2008). Indeed, creative people are better able to activate and maintain the activation of subordinate meanings after being exposed to an ambiguous word (Atchley, Keeney, & Burgess, 1999). If so, the training effect, which is reflected as enhancing the activation of less salient concepts, may affect the participants' creative abilities. The possible transfer of the training to creative thinking, among other tasks that are underlined by coarse semantic processing, should be examined in future studies, that will further evaluate the effectiveness of this training under additional contexts, and in additional untrained tasks, including more ecological tests for using semantic processing in daily life.

Together with the enhanced semantic performance, we observed changes in prefrontal asymmetry along with the training by using a behavioral laterality measure. The cognitive enhancement and the shift in laterality indices correlated, implying that the semantic performance changes evident in the linguistic task are indeed grounded in right hemisphere processes, and were not an irrelevant by-product of the training. Previously, Erickson and his colleagues (Erickson et al., 2007) observed prefrontal asymmetry shifts that were induced by cognitive training by using direct neuroimaging measures (fMRI evidence). The authors found correlations between performance improvement in trained attention abilities and the asymmetry shifts, and interpreted it as evidence for a more efficient utilization of proper strategies that was induced by the training By the same token, it is plausible to interpret the correlation that was found in our study, albeit the use of an indirect behavioral marker for the asymmetry shifts, which is evident in the effective recruitment of right hemisphere semantic processes. Moreover, by demonstrating that training the skills of coarse activation, integration and selection yielded changes in RH bias which predicted the extent of the training-induced improvement in processing distant meanings, our findings provide strong support to the empirical and theoretical grounds for this study (e.g., Jung-Beeman, 2005).

As opposed to the training group, where RH bias predicted the post-training semantic improvement, in the control group laterality bias did not significantly predict the post-training individual changes. Nonetheless, the post-training change in the control group was predicted by the participants' reward sensitivity, so that participants with higher reward responsiveness showed greater improvement at the second assessment. This finding is in line with predictions derived from the reinforcement sensitivity theory (Pickering & Gray, 1999), that participants with high BAS related tendencies will display superior learning when their behavior is rewarded (Smillie, Dalgleish, & Jackson, 2007). Interestingly, in the training group, motivational tendencies did not predict this change; hence training-induced semantic improvement did not stem from mere motivation and reward sensitivity.

Since the training achieved the desired semantic effect at the group level, we aimed to further evaluate the individual differences that may affect the extent to which participants can benefit from RH semantic training. Many methodological discussions in the field of cognitive training deliberate on the need to better understand what individual characteristics affect the training gain (e.g., Blume et al., 2010; Willis, 2010). As seen in FIG. 4, our results clearly show that participants with a better starting point in terms of prior linguistic capabilities (as measured externally by the verbal PET score) benefited more from the training. Complemented by the finding that prior verbal abilities did not significantly predict improvement in the second assessment among the control group, it is clear that the training effect was moderated by the participants' prior linguistic abilities.

Pre-training cognitive abilities has been long recognized as one of the most important moderators of training gain and transfer: "What the learner brings to the instructional situation in prior knowledge and cognitive skills is of crucial importance" (Pintrich, Cross, Kozma, & McKeachie, 1986, p. 613). Recently, in a meta-analysis of 89 training empirical studies, Blume and his colleagues found that cognitive abilities were the best predictor of transfer, compared to other personality and motivation factors (Blume et al., 2010). Accordingly, we suspect that the training demands in our study were too high for participants with lower linguistic abilities such as vocabulary and verbal reasoning. Previous studies have shown that when training task is perceived as too effortful and difficult (rather than challenging), the performance in the training itself, and consequently the transfer, are at stake (Jaeggi, Buschkuehl, Jonides, & Shah, 2011). If so, employing an adaptive training program, which is tailored to each participant's prior abilities and training progress, may extend training benefits to a broader spectrum of participants with varied prior abilities (for example, see the adaptive working memory training programs as reviewed by Shipstead, Redick, & Engle, 2010).

Alternatively, the provided feedback may have not been supportive enough for some of the participants. Recently, it has been demonstrated that cognitive resources have an influence on a participant's absorption of feedback (Kelley & Collins McLaughlin, 2012). Participants with lower cognitive resources (i.e., older adults as opposed to younger adults) were less able to utilize low support feedback, including only KR, and learned only by means of clear error feedback which explicated the rules to be learned. As PET scores reflect verbal reasoning, among the rest, it is possible that people with lower verbal reasoning skills were less able to generalize the provided feedback and modify their semantic strategies accordingly, as opposed to others who sufficed with the provided feedback and were able to improve their skills based on it. That is, the verbal reasoning abilities could mediate the effect of feedback. Future studies could manipulate the feedback level and see if it contributes to improvement in training, and whether improved training performance will lead to enhanced transfer (or rather to decreased transfer, as can be predicted based on Schmidt and Bjork, 1992).

Alongside the strong evidence for the primary training effect (i.e., the semantic enhancement), our results might also be interpreted as preliminary evidence for a secondary effect on memory, which demonstrates a positive side effect of the training. The basic task in both programs, training and control, demanded some use of working memory in order to integrate verbal information from different clues, as the clues' content was not continuously presented on screen. And indeed, both groups showed some improvement following the training in the different memory measurements—while no such improvement was expected, as these measurements are considered to have high test-retest reliability (Geffen, 1994). It is possible then, that both programs had a positive artifact on verbal memory.

For the sake of comparison, when test-retest reliability was tested using two English equivalent versions of this task, significant correlations were found between best memory and total memory scores in two sessions that were separated by 6-14 days (Geffen, 1994). In our study, no such correlations were found in the best memory score (with almost half of the participants showing improvement—14/30, and 11/30 showing no change). Also, no correlation was found in the training group when using the total memory score (with 10/15 of each group showing slight improvement following training) Moreover, the average improvement in our study was 2.5 times larger than observed in the Geffen study for the best memory score, and 4.6 times larger than the total memory score. Hence, this comparison supports the interpretation that the improvement in the memory scores observed in both groups does not stem from an ordinary practice effect, but rather represents an enhancement in verbal memory following both the training and control programs. In order to be confirmed, this effect should be further evaluated with an additional passive control group that will perform the same assessments on the same schedule without any intervention. Nonetheless, this early finding can be taken to imply that the semantic training program had a possible secondary effect on memory.

If so, in accordance with our primary and secondary goals, we have been able to show that healthy adults can somewhat improve their semantic performance, and perhaps memory performance too, by using our training program. Our third objective in this study went beyond its applied aspects, which intended to deepen our understanding on semantic processing in the right hemisphere by testing whether these skills could be trained selectively, in isolation from more general linguistic and non-linguistic processes. According to our predictions, the training-induced effect was not transferred to non-semantic skills, as evident by the lack of improvement in other verbal and non-verbal tasks. Hence, the semantic improvement was not an artifact of a more general improvement in verbal and non-verbal skills, whether in the RH or in general. This comes to show that semantic processes among healthy literate adults can be trained, per se.

As traces for additional training benefits were evident in verbal memory, the question remains whether the semantic enhancement was mediated by verbal memory enhancement. The training emphasized the retention of multiple meanings for their later integration. While BAIS model considers the maintenance of the activation of remote meanings for longer periods of time to be part of the diffuse qualities of coarse semantic activation (Jung-Beeman, 2005), it is possible that our training utilized other verbal memory skills in order to retain the activation of these meanings. However, as both groups exhibited the memory benefits, and only the training group exhibited the semantic benefit, it is unlikely that enhancement in verbal memory underlies observed enhancement in semantic processing. Moreover, correlations between the individual post-training changes in the semantic and memory scores were not significant for neither group nor beyond the group. Nonetheless, the task that was used in this study to evaluate semantic enhancement utilized an intermediate interstimulus interval (ISI=500 ms), so that we tested meaning retention as part of the semantic judgments for less than a second. In that time frame, we can conclude that meaning retention does not depend on verbal memory; however, more studies are necessary in order to determine the underlying processes of meaning retention for longer periods of time.

Lastly, while significant improvement was evident in response to distant meanings, a marginally significant improvement was also noticed in responses to salient meanings, a performance change which is known to reflect LH dominated semantic processes (Giora & Strinaris, 2009). Nonetheless, our findings can be interpreted to show some dissociation between these effects: first, the lack of correlation between the individual changes in these two conditions among the training participants (as opposed to a high correlation among the control participants), suggests that these effects are somewhat independent; and indeed, the LH related effect was not predicted by laterality shifts, as opposed to the RH related one, nor was it predicted by prior verbal abilities.

These findings are in line with various accounts of lateralization of semantic processing that emphasize the different processes in each hemisphere in light of interhemispheric collaboration, e.g., the PARLO framework (Federmeier, 2007) and BAIS model (Jung-Beeman, 2005). Empirical evidence supports these accounts by showing the cooperation of both hemispheres in processing linguistic stimuli (e.g., Banich & Belger, 1990; Weissman & Banich, 2000; Welcome & Chiarello, 2008). In accordance with this evidence, it is not surprising that the semantic training program stimulated LH semantic processing too; but most importantly, the interpretation of the co-occurring changes in the different conditions of the semantic task as independent training-induced changes in RH and LH semantic processing provides additional support for these models from a new and applied perspective. In addition, on the practical level these findings indicate that our training program may have had another positive artifact on semantic processes in addition to the targeted coarse semantic skills. To further explore this conclusion, future studies could employ direct online brain imaging measurements and monitor the lateralization patterns throughout the training and during the assessment.

Thus, this controlled study demonstrated the effective enhancement of semantic processes in the right hemisphere by means of non-invasive semantic training. Additional benefits may appear following the training in semantic processing in the left hemisphere and in verbal memory. In a broader context, our findings serve as a successful application of theories and empirical data in the field of cognitive neuroscience which selectively improve cognitive performance. Finally, while our primary research goal was to apply the current knowledge on semantic processes in the right hemisphere, our findings also enhance our understanding of these processes. By showing that the semantic processing of distant meanings could be selectively enhanced and that this performance change is correlated with laterality shifts in RH bias, this study provides additional support to the unique role that the right hemisphere plays in semantic processing.

REFERENCES

Abdullaev, Y. G., & Posner, M. I. (1997). Time Course of Activating Brain Areas in Generating Verbal Associations. *Psychological Science*, 8(1), 56-59. SAGE Publications.
Atchley, R. A., Keeney, M., & Burgess, C. (1999). Cerebral hemispheric mechanisms linking ambiguous word meaning retrieval and creativity. *Brain and Cognition*, 40(3), 479-499.
Balota, D. A., & Chumbley, J. I. (1984). Are lexical decisions a good measure of lexical access? The role of word frequency in the neglected decision stage. *Journal of Experimental Psychology: Human Perception and Performance*, 10(3), 340-357.
Banich, M. T., & Belger, A. (1990). Interhemispheric interaction: How do the hemispheres divide and conquer a task? *Cortex*, 26(1), 77-94.
Barnett, S. M., & Ceci, S. J. (2002). When and where do we apply what we learn?: A taxonomy for far transfer. *Psychological Bulletin*, 128(4), 612-637.
Beeman, M. (1998). Coarse semantic coding and discourse comprehension. In M. Beeman & C. Chiarello (Eds.), *Right Hemisphere Language Comprehension: Perspectives from Cognitive Neuroscience* (pp. 255-284). Mahwah, N.J.: Erlbaum.
Beeman, M., & Chiarello, C. (1998). *Right Hemisphere Language Comprehension: Perspectives from Cognitive Neuroscience*. Mahwah: Lawrence Erlbaum Associates Publishers.
Beeman, M., Friedman, R. B., Grafman, J., Perez, E., Diamond, S., & Lindsay, M. B. (1994). Summation Priming and Coarse Semantic Coding in the Right Hemisphere. *Journal of Cognitive Neuroscience*, 6(1), 26-45.
Beller, M. (1994). Psychometric and Social Issues in Admissions to Israeli Universities. *Educational Measurement: Issues and Practice*, 13(2), 12-20.
Beller, M. (1995). Translated versions of Israel's interuniversity Psychometric Entrance Test (PET). In T. Oakland & R. K. Hambleton (Eds.), *International Perspectives on Academic Assessment* (pp. 207-218). Boston: Kluwer.
Berkeley, S., Scruggs, T. E., & Mastropieri, M. A. (2009). Reading Comprehension Instruction for Students With Learning Disabilities, 1995-2006: A Meta-Analysis. *Remedial and Special Education*, 31(6), 423-436.
Blake, M. L. (2010). Communication Deficits Associated with Right Hemisphere Brain Damage. In J. S. Damico, N. Müller, & M. J. Ball (Eds.), *The Handbook of Language and Speech Disorders* (pp. 556-576). Oxford, UK: Wiley-Blackwell.
Blok, H., Oostdam, R., Otter, M. E., & Overmaat, M. (2002). Computer-Assisted Instruction in Support of Beginning Reading Instruction: A Review. *Review of Educational Research*, 72(1), 101-130.
Blume, B. D., Ford, J. K., Baldwin, T. T., & Huang, J. L. (2010). Transfer of Training: A Meta-Analytic Review. *Journal of Management*, 36(4), 1065-1105.
Bourne, V. J. (2006). The divided visual field paradigm: methodological considerations. *Laterality*, 11(4), 373-393.
Brown, A. S., & Mitchell, D. B. (1994). A reevaluation of semantic versus nonsemantic processing in implicit memory. *Memory & Cognition*, 22(5), 533-541.
Burgess, C., & Simpson, G. B. (1988). Cerebral hemispheric mechanisms in the retrieval of ambiguous word meanings *Brain and Language*, 33(1), 86-103.
Buschkuehl, M., & Jaeggi, S. M. (2010). Improving intelligence: a literature review. *Swiss Medical Weekly*, 140 (19-20), 266-272.
Campbell, D. T., & Stanley, J. C. (1963). *Experimental and Quasi-Experimental Designs for Research*. (N. L. Gage, Ed.). Chicago, Ill.: Rand-McNally.
Carver, C. S., & White, T. L. (1994). Behavioral inhibition, behavioral activation, and affective responses to impending reward and punishment: The BIS/BAS Scales. *Journal of Personality and Social Psychology*, 67(2), 319-333.
Coltheart, M. (2006). Dual route and connectionist models of reading: an overview. *London Review of Education*, 4(1), 5-17. Routledge.
Cornelissen, K., Laine, M., Tarkiainen, A., Järvensivu, T., Martin, N., & Salmelin, R. (2003). Adult brain plasticity elicited by anomia treatment. *Journal of Cognitive Neuroscience*, 15(3), 444-461.
Coulson, S., & Wu, Y. C. (2005). Right hemisphere activation of joke-related information: an event-related brain potential study. *Journal of Cognitive Neuroscience*, 17(3), 494-506.
Cousineau, D. (2005). Confidence intervals in within-subject designs: A simpler solution to Loftus and Masson's method. *Tutorial in Quantitative Methods for Psychology*, 1(1), 42-45.
Craik, F. I. M., & Lockhart, R. S. (1972). Levels of processing: A framework for memory research. *Journal of Verbal Learning and Verbal Behavior*, 11(6), 671-684.

Dahlin, E., Neely, A. S., Larsson, A., Bäckman, L., & Nyberg, L. (2008). Transfer of learning after updating training mediated by the striatum. *Science,* 320, 1510-1512.

Dien, J. (2008). Looking both ways through time: the Janus model of lateralized cognition. *Brain and Cognition,* 67(3), 292-323.

Edmonds, M. S., Vaughn, S., Wexler, J., Reutebuch, C., Cable, A., Tackett, K. K., & Schnakenberg, J. W. (2009). A Synthesis of Reading Interventions and Effects on Reading Comprehension Outcomes for Older Struggling Readers. *Review of Educational Research,* 79(1), 262-300.

Erickson, K. I., Colcombe, S. J., Wadhwa, R., Bherer, L., Peterson, M. S., Scalf, P. E., Kim, J. S., et al. (2007). Training-induced plasticity in older adults: effects of training on hemispheric asymmetry. *Neurobiology of Aging,* 28(2), 272-283.

Faust, M., & Kahana, A. (2002). Priming summation in the cerebral hemispheres: evidence from semantically convergent and semantically divergent primes. *Neuropsychologia,* 40(7), 892-901.

Federmeier, K. D. (2007). Thinking ahead: the role and roots of prediction in language comprehension. *Psychophysiology,* 44(4), 491-505.

Geffen, G. (1994). Test-retest reliability of a new form of the auditory verbal learning test (AVLT). *Archives of Clinical Neuropsychology,* 9(4), 303-316.

Giora, R., & Stringaris, K. A. (2009). Neural substrates of metaphor. In P. Hogan (Ed.), *The Cambridge Encyclopedia of the Language Sciences* (pp. 489-492). Cambridge, UK: Cambridge University Press.

Gopher, D. (2007). Emphasis Changes as a Training Protocol for High-Demand Tasks. In A. F. Kramer, D. Woegmann, & A. Kirlik (Eds.), *Attention: from Theory to Practice* (Vol. 101, pp. 209-224). Oxford University Press.

Gopher, D., Weil, M., & Bareket, T. (1994). Transfer of a skill from a computer game trainer to flight. *Human Factors,* 36(3), 387-405.

Gopher, D., Weil, M., & Siegel, D. (1989). Practice under changing priorities: An approach to training of complex skills. *Acta Psychologica,* 71, 147-177.

Green, C. S., & Bavelier, D. (2008). Exercising your brain: a review of human brain plasticity and training-induced learning. *Psychology and Aging,* 23(4), 692-701.

Harpaz, Y., Levkovitz, Y., & Lavidor, M. (2009). Lexical ambiguity resolution in Wernicke's area and its right homologue. *Cortex,* 45(9), 1097-1103.

Hart, S. G., & Battiste, V. (1992). Field test of video game trainer. *Proceedings of the Human Factors Society 36th Annual Meeting* (pp. 1291-1295).

Hudson, P. T., & Bergman, M. W. (1985). Lexical knowledge in word recognition: Word length and word frequency in naming and lexical decision tasks. *Journal of Memory and Language,* 24(1), 46-58.

Jaeggi, S. M., Buschkuehl, M., Jonides, J., & Shah, P. (2011). Short- and long-term benefits of cognitive training. *Proceedings of the National Academy of Sciences of the United States of America,* 108(25), 10081-10086.

Jean, L., Bergeron, M.-E., Thivierge, S., & Simard, M. (2010). Cognitive Intervention Programs for Individuals With Mild Cognitive Impairment: Systematic Review of the Literature. *The American Journal of Geriatric Psychiatry,* 18(4), 281-296.

Jewell, G., & McCourt, M. E. (2000). Pseudoneglect: a review and meta-analysis of performance factors in line bisection tasks. *Neuropsychologia,* 38(1), 93-110.

Jung-Beeman, M. (2005). Bilateral brain processes for comprehending natural language. *Trends in Cognitive Sciences,* 9(11), 512-518.

Jung-Beeman, M., Bowden, E. M., & Gernsbacher, M. A. (2000). Right and left hemisphere cooperation for drawing predictive and coherence inferences during normal story comprehension. *Brain and Language,* 71(2), 310-336.

Jung-Beeman, M., Bowden, E. M., Haberman, J., Frymiare, J. L., Arambel-Liu, S., Greenblatt, R., Reber, P. J., et al. (2004). Neural activity when people solve verbal problems with insight. *PLoS Biology,* 2(4), 500-510. Public Library of Science.

Kahlaoui, K., Scherer, L. C., & Joanette, Y. (2008). The Right Hemisphere's Contribution to the Processing of Semantic Relationships between Words. *Language and Linguistics Compass,* 2(4), 550-568.

Kelley, C. M., & Collins McLaughlin, A. (2012). Individual Differences in the Benefits of Feedback for Learning. *Human Factors: The Journal of the Human Factors and Ergonomics Society,* 54(1), 26-35.

Kiefer, M., Weisbrod, M., Kern, I., Maier, S., & Spitzer, M. (1998). Right hemisphere activation during indirect semantic priming: evidence from event-related potentials. *Brain and Language,* 64(3), 377-408.

Kircher, T. T., Brammer, M., Tous Andreu, N., Williams, S. C., & McGuire, P. K. (2001). Engagement of right temporal cortex during processing of linguistic context. *Neuropsychologia,* 39(8), 798-809.

Levy, T., Walsh, V., & Lavidor, M. (2010). Dorsal stream modulation of visual word recognition in skilled readers. *Vision Research,* 50(9), 883-888.

Lezak, M. D. (1983). *Neuropsychological Assessment* (2nd ed.). New York: Oxford University Press.

Lindell, A. K. (2006). In your right mind: right hemisphere contributions to language processing and production. *Neuropsychology Review,* 16(3), 131-148.

Lundgren, K., Brownell, H., Cayer-meade, C., Milione, J., & Kearns, K. (2011). Treating metaphor interpretation deficits subsequent to right hemisphere brain damage: Preliminary results. *Aphasiology,* 25(4), 456-474.

Marinkovic, K., Baldwin, S., Courtney, M. G., Witzel, T., Dale, A. M., & Halgren, E. (2011). Right hemisphere has the last laugh: neural dynamics of joke appreciation. *Cognitive, Affective & Behavioral Neuroscience,* 11(1), 113-130. Springer New York.

Mashal, N., Faust, M., Hendler, T., & Jung-Beeman, M. (2007). An fMRI investigation of the neural correlates underlying the processing of novel metaphoric expressions. *Brain and Language,* 100(2), 115-126.

Mashal, N., Faust, M., Hendler, T., & Jung-Beeman, M. (2008). Hemispheric differences in processing the literal interpretation of idioms: converging evidence from behavioral and fMRI studies. *Cortex,* 44(7), 848-860.

Mashal, N., Faust, M., Hendler, T., & Jung-Beeman, M. (2009). An fMRI study of processing novel metaphoric sentences. *Laterality,* 14(1), 30-54.

McGurk, S. R., Twamley, E. W., Sitzer, D. I., McHugo, G. J., & Mueser, K. T. (2007). A meta-analysis of cognitive remediation in schizophrenia. *The American Journal of Psychiatry,* 164(12), 1791-1802.

McNab, F., Varrone, A., Farde, L., Jucaite, A., Bystritsky, P., Forssberg, H., & Klingberg, T. (2009). Changes in cortical dopamine D1 receptor binding associated with cognitive training. *Science*, 323, 800-802.

Melby-Lervåg, M., & Hulme, C. (2012). Is Working Memory Training Effective? A Meta-Analytic Review. *Developmental Psychology*, Advance online publication.

Mitchell, R. L. C., & Crow, T. J. (2005). Right hemisphere language functions and schizophrenia: the forgotten hemisphere? *Brain: a Journal of Neurology*, 128(5), 963-978.

Nash, K., McGregor, I., & Inzlicht, M. (2010). Line bisection as a neural marker of approach motivation. *Psychophysiology*, 47(5), 979-983.

Oldfield, R. C. C. (1971). The assessment and analysis of handedness: the Edinburgh inventory. *Neuropsychologia*, 9(1), 97-113.

Olesen, P. J., Westerberg, H., & Klingberg, T. (2004). Increased prefrontal and parietal activity after training of working memory. *Nature Neuroscience*, 7(1), 75-79.

Peleg, O., & Eviatar, Z. (2008). Hemispheric sensitivities to lexical and contextual information: evidence from lexical ambiguity resolution. *Brain and Language*, 105(2), 71-82.

Peleg, O., & Eviatar, Z. (2009). Semantic asymmetries are modulated by phonological asymmetries: evidence from the disambiguation of homophonic versus heterophonic homographs. *Brain and Cognition*, 70(1), 154-62.

Peleg, O., & Eviatar, Z. (2012). Understanding written words: Phonological, lexical and Contextual Effects in the Two Cerebral Hemispheres. In M. Faust (Ed.), *The Handbook of the Neuropsychology of Language* (pp. 59-76). West Sussex, UK: John Wiley and Sons Ltd.

Peretz, Y., & Lavidor, M. (in press). Enhancing lexical ambiguity resolution by brain polarization of the right posterior superior temporal sulcus. *Cortex*.

Pickering, A. D., & Gray, J. A. (1999). The neuroscience of personality. In L. A. Pervin & O. P. John (Eds.), *Handbook of Personality: Theory and Research* (2nd ed., Vol. 2, pp. 277-299). New York, N.Y.: Guilford Press.

Pintrich, P. R., Cross, D. R., Kozma, R. B., & McKeachie, W. J. (1986). Instructional psychology. *Annual Review of Psychology*, 37, 611-651.

Rey, A. (1941). L'examen psychologie dans les cas d'encephalopathie traumatique. *Archives de Psychologie*, 28, 286-340.

Rey, A. (1964). *L'Examen Clinique en Psychologie*. Paris: Presses Universitaires de France.

Ron Nelson, J., Benner, G. J., & Gonzalez, J. (2003). Learner Characteristics that Influence the Treatment Effectiveness of Early Literacy Interventions: A Meta-Analytic Review. *Learning Disabilities Research and Practice*, 18(4), 255-267.

Sass, K., Krach, S., Sachs, O., & Kircher, T. (2009). Lion-tiger-stripes: Neural correlates of indirect semantic priming across processing modalities. *NeuroImage*, 45(1), 224-236.

Schmidt, B. R. A., & Bjork, R. A. (1992). New Conceptualizations of Practice: Common Principles in Three Paradigms Suggest New Concepts for Training. *Psychological Science*, 3(4), 207-218.

Seger, C. A., Desmond, J. E., Glover, G. H., & Gabrieli, J. D. E. (2000). Functional magnetic resonance imaging evidence for right-hemisphere involvement in processing unusual semantic relationships. *Neuropsychology*, 14(3), 361-369.

Shalev, L., Tsal, Y., & Mevorach, C. (2007). Computerized progressive attentional training (CPAT) program: effective direct intervention for children with ADHD. *Child Neuropsychology*, 13(4), 382-388.

Shipstead, Z., Redick, T. S., & Engle, R. W. (2010). Does working memory training generalize? *Psychologica Belgica*, 50, 3(4), 245-276. Academia Press.

Shute, V. J. (2008). Focus on Formative Feedback. *Review of Educational Research*, 78(1), 153-189.

Smillie, L. D., Dalgleish, L. I., & Jackson, C. J. (2007). Distinguishing between learning and motivation in behavioral tests of the reinforcement sensitivity theory of personality. *Personality & Social Psychology Bulletin*, 33(4), 476-489.

Smith, G. E., Housen, P., Yaffe, K., Ruff, R., Kennison, R. F., Mahncke, H. W., & Zelinski, E. M. (2009). A cognitive training program based on principles of brain plasticity: results from the Improvement in Memory with Plasticity-based Adaptive Cognitive Training (IMPACT) study. *Journal of the American Geriatrics Society*, 57(4), 594-603.

St George, M., Kutas, M., Martinez, A., & Sereno, M. I. (1999). Semantic integration in reading: engagement of the right hemisphere during discourse processing. *Brain*, 122, 1317-1325.

Tegano, D. W. (1990). Relationship of tolerance of ambiguity and playfulness to creativity. *Psychological Reports*, 66, 1047-1056.

Tompkins, C. A., Baumgaertner, A., Blake, M. L., & Fassbinder, W. (2000). Mechanisms of discourse comprehension impairment after right hemisphere brain damage: suppression in lexical ambiguity resolution. *Journal of Speech, Language, and Hearing Research: JSLHR*, 43(1), 62-78.

Tompkins, C. A., Blake, M. T., Wambaugh, J., & Meigh, K. (2011). A novel, implicit treatment for language comprehension processes in right hemisphere brain damage: Phase I data. *Aphasiology*, 25(6-7), 789-799.

Tompkins, C. A., Fassbinder, W., Scharp, V. L., & Meigh, K. M. (2008). Activation and maintenance of peripheral semantic features of unambiguous words after right hemisphere brain damage in adults. *Aphasiology*, 22(2), 119-138.

Tompkins, C. A., Scharp, V. L., Meigh, K. M., & Fassbinder, W. (2008). Coarse coding and discourse comprehension in adults with right hemisphere brain damage. *Aphasiology*, 22(2), 204-223.

Toplak, M. E., Connors, L., Shuster, J., Knezevic, B., & Parks, S. (2008). Review of cognitive, cognitive-behavioral, and neural-based interventions for Attention-Deficit/Hyperactivity Disorder (ADHD). *Clinical Psychology Review*, 28(5), 801-823.

Twamley, E. W., Jeste, D. V., & Bellack, A. S. (2003). A review of cognitive training in schizophrenia. *Schizophrenia Bulletin*, 29(2), 359-382.

Vakil, E., & Blachstein, H. (1993). Rey Auditory-Verbal Learning Test: Structure analysis. *Journal of Clinical Psychology*, 49(6), 883-890.

Vakil, E., & Blachstein, H. (1997). Rey AVLT: Developmental norms for adults and the sensitivity of different memory measures to age. *The Clinical Neuropsychologist*, 11(4), 356-369.

Valenzuela, M., & Sachdev, P. (2009). Can cognitive training prevent the onset of dementia? A systematic review of randomized clinical trials with longitudinal follow up. *Alzheimer's & Dementia: The Journal of the Alzheimer's*, 5(4), 157-158.

Virtue, S., Parrish, T., & Jung-Beeman, M. (2008). Inferences during story comprehension: cortical recruitment affected by predictability of events and working memory capacity. *Journal of Cognitive Neuroscience,* 20(12), 2274-2284.

Weissman, D. H., & Banich, M. T. (2000). The cerebral hemispheres cooperate to perform complex but not simple tasks. *Neuropsychology,* 14(1), 41-59.

Welcome, S. E., & Chiarello, C. (2008). How dynamic is interhemispheric interaction? Effects of task switching on the across-hemisphere advantage. *Brain and Cognition,* 67(1), 69-75.

Willis, S. L. (2010). Cognitive Plasticity: Findings from Cognitive Training Studies. *Annual Report of Meiso University,* 28, 37-49.

Willis, S. L., Tennstedt, S. L., Marsiske, M., Ball, K., Elias, J., Koepke, K. M., Morris, J. N., et al. (2006). Long-term effects of cognitive training on everyday functional outcomes in older adults. *JAMA: the Journal of the American Medical Association,* 296(23), 2805-2814.

Yechiam, E., Erev, I., & Gopher, D. (2001). On the potential value and limitations of emphasis change and other exploration-enhancing training methods. *Journal of Experimental Psychology—Applied,* 7(4), 277-285.

Zenasni, F., Besançon, M., & Lubart, T. (2008). Creativity and Tolerance of Ambiguity: An Empirical Study. *The Journal of Creative Behavior,* 42(1), 61-73.

Çiçek, M., Nalçaci, E., & Kalaycioglu, C. (2003). Line bisection task performance and resting EEG alpha power. *International Journal of Neuroscience,* 113(6), 849-866.

The present invention has been described and embodiments provided relating to the above described methods and systems. The present invention is now further described by the claims which follow. Optionally, any of the above embodiments or sub-embodiments described herein may be combined to form a combination or sub-combination.

What is claimed is:

1. A method for training a semantic ability of a subject, the method being performed by a computer, the method comprising:
   a. displaying a linguistic task to a subject on a display of the computer, said linguistic task comprising providing one or more words, wherein said linguistic task is directed to training the subject in a specific semantic skill or skills;
   b. providing a plurality of linguistic clues to the subject, through the display of the computer, said plurality of linguistic clues comprising content capable of activating concepts related to said one or more words but wherein said content does not include said one or more words or synonyms thereof, wherein said linguistic clues are selected such that the subject integrates said plurality of linguistic clues to solve said linguistic task, wherein said linguistic clue comprises an image, audio, video, text or a combination thereof;
   c. receiving a solution to said linguistic task by the subject through the computer; and
   d. when said solution is not correct, providing one or more additional linguistic clues to the subject, said one or more additional linguistic clues comprising content capable of activating concepts related to said one or more words, wherein the subject integrates said one or more additional linguistic clues with said plurality of linguistic clues to solve said linguistic task, and wherein i) said content does not include said one or more words or synonyms thereof, or ii) when said content does include said one or more words or synonyms thereof, said content does not comprise written text;
   wherein said plurality of clues is revealed sequentially according to a requirement for integration of said plurality of linguistic clues by the subject;
   wherein each clue is revealed separately, such that only one clue is revealed at a given time; wherein said providing said linguistic clues to the subject further comprises penalizing the subject when the subject requests display of a previously displayed clue.

2. The method of claim 1, wherein said providing one or more words by the subject comprises at least one of entering said one or more words to the computer and identifying said one or more words by the subject.

3. The method of claim 1, wherein said receiving said solution to said linguistic task comprises analyzing said solution and wherein said analyzing said solution further comprises analyzing a correctness of said solution and one or more of a time required to complete said solution, a number of clues provided to the subject before said solution is submitted, a number of guesses before the correct solution was submitted, a number of times previously seen clues were displayed again, or a combination thereof.

4. The method of claim 1, comprising repeating stages a-d at least once; wherein at least one of said linguistic task and said at least one linguistic clue is different upon repetition of stages a-d.

5. The method of claim 1, wherein said providing said plurality of linguistic clues to the subject, through the display of the computer, further comprises selecting said linguistic clues according to a level of difficulty; wherein said level of difficulty is determined according to a semantic ability of the subject.

6. The method of claim 1, wherein said selecting said linguistic clues further comprises
   selecting a game world for the subject, said game world having a plurality of characteristic features, including at least one or more of instructions, incentives, type of clues, penalty on display of previous clues, sequence of clues and time of exposure of a given clue; and
   selecting said linguistic clues also according to said game world.

7. The method of claim 1, further comprising providing an incentive to the subject to provide said solution through the computer; wherein said incentive comprises one or more of points to obtain a reward, points convertible to monetary value, points relating to progress and/or points for comparison between different users.

8. A method for determining semantic ability of a subject, the method being performed by a computer, the method comprising:
   displaying a linguistic task to the subject on a display of the computer, said linguistic task comprising providing one or more words by the subject to the computer;
   providing at least one linguistic clue to the subject, through the display of the computer, said at least one linguistic clue comprising content capable of activating concepts related to said one or more words but wherein i) said content does not include said one or more words or synonyms thereof, or ii) when said content does include said one or more words or synonyms thereof, said content does not comprise written text, wherein said linguistic clue comprises an image, audio, video, text or a combination thereof, and wherein said linguistic clues are selected such that the subject integrates said at least one to solve said linguistic task;
   receiving a solution to said linguistic task by the subject through the computer; and analyzing said solution to determine the semantic ability of the subject;
wherein said analyzing said solution further comprises analyzing a correctness of said solution and one or more of a time required to complete said solution or a number of clues provided to the subject before said solution is submitted.

9. The method of claim 8, comprising repeating the displaying, the providing, the receiving, and the analyzing at least once; wherein said linguistic task and said at least one linguistic du upon repetition are different.

10. The method of claim 8, wherein said providing said at least one to the subject, through the display of the computer, further comprises selecting said linguistic clues according to a semantic ability of the subject to be improved.

11. The method of claim 8, wherein said selecting said linguistic clues further comprises selecting a game world for the subject, said game world having a plurality of characteristic features, including at least one or more of instructions, incentives, type of clues, penalty on display of previous clues, sequence of clues and time of exposure of a given clue; and selecting said linguistic clues also according to said game world.

12. A method for training a semantic ability of a subject, the method being performed by a computer, the method comprising:
   a. displaying a linguistic task to the subject on a display of the computer, said linguistic task comprising providing one or more words;
   b. providing at least one linguistic clue to the subject, through the display of the computer, said at least one linguistic clue comprising content capable of activating concepts related to said one or more words but wherein said content does not include said one or more words or synonyms thereof, wherein said linguistic clue comprises an image, audio, video, text, or a combination thereof;
   c. receiving a solution to said linguistic task by the subject through the computer; and
   d. when said solutions is not correct, providing one or more additional linguistic clues to the subject, said one or more additional linguistic clues comprising content capable of activating concepts related to said one or more words but wherein
   i) said content does not include said one or more words or synonyms thereof, or
   ii) when said content does include said one or more words or synonyms thereof, said content does not comprise written text;
   e. analyzing a semantic ability of the subject through the computer according to a diagnostic test and selecting said linguistic task to match said semantic ability.

13. The method of claim 12, further comprising e. repeating stages a-d at least once.

* * * * *